(12) United States Patent
Han et al.

(10) Patent No.: US 11,158,809 B2
(45) Date of Patent: Oct. 26, 2021

(54) LIGHT ABSORBER AND ORGANIC ELECTROLUMINESCENCE DEVICE INCLUDING THE SAME

(71) Applicant: Samsung Display Co., Ltd., Yongin-si (KR)

(72) Inventors: Sanghyun Han, Hwaseong-si (KR); Wonmin Yun, Yongin-si (KR); Jongwoo Kim, Hwaseong-si (KR); Jangyeol Baek, Yongin-si (KR); Eunjae Jeong, Hwaseong-si (KR); Yohan Kim, Seoul (KR); Yisu Kim, Seoul (KR); Youngkook Kim, Suwon-si (KR); Seokhwan Hwang, Suwon-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 357 days.

(21) Appl. No.: 16/176,876

(22) Filed: Oct. 31, 2018

(65) Prior Publication Data
US 2019/0131532 A1  May 2, 2019

(30) Foreign Application Priority Data

Oct. 31, 2017 (KR) .................. 10-2017-0144168
Mar. 6, 2018 (KR) .................. 10-2018-0026152

(51) Int. Cl.
*H01L 51/00* (2006.01)
*C07C 49/788* (2006.01)
(Continued)

(52) U.S. Cl.
CPC ........ *H01L 51/0054* (2013.01); *C07C 49/784* (2013.01); *C07C 49/788* (2013.01);
(Continued)

(58) Field of Classification Search
CPC ............ H01L 51/0054; H01L 51/0052; H01L 51/0073; H01L 51/0074; H01L 51/5284;
(Continued)

(56) References Cited

U.S. PATENT DOCUMENTS 5,677,112 A * 10/1997 Urano et al. ............ G03F 7/091
430/325
9,093,585 B2   7/2015 Seo et al.
(Continued)

FOREIGN PATENT DOCUMENTS

JP      52-28793      7/1977
JP      2000-119261 A   4/2000
(Continued)

OTHER PUBLICATIONS

Maeda, Hajime et al.; "Photo-Fries rearrangement of 1-pyrenyl esters"; Tetrahedron Letters; 58; 2017; pp. 4377-4380.
(Continued)

*Primary Examiner* — Shane Fang
(74) *Attorney, Agent, or Firm* — Lewis Roca Rothgerber Christie LLP

(57) ABSTRACT

Provided is an organic electroluminescence device provided with a light absorber represented by Formula 1 below, and a light absorbing layer including the same. In Formula 1, Ar is pyrene, chrysene, or anthracene, and Y is a hydrogen atom or a substituent, and X is represented by any one of Formula 2-1 to 2-3 below.

(Continued)

Formula 1

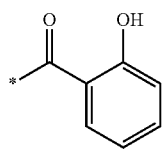

Formula 2-1

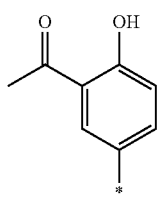

Formula 2-2

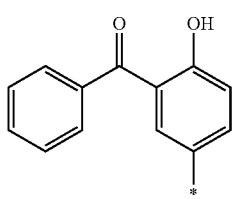

Formula 2-3

24 Claims, 3 Drawing Sheets

(51) Int. Cl.
| C07C 49/784 | (2006.01) |
| H01L 51/52 | (2006.01) |
| C07C 15/38 | (2006.01) |
| H01L 51/42 | (2006.01) |
| H01L 51/50 | (2006.01) |
| C07C 15/24 | (2006.01) |

(52) U.S. Cl.
CPC ...... *H01L 51/0052* (2013.01); *H01L 51/0073* (2013.01); *H01L 51/0074* (2013.01); *H01L 51/5284* (2013.01); *C07C 15/24* (2013.01); *C07C 15/38* (2013.01); *H01L 51/42* (2013.01); *H01L 51/50* (2013.01); *H01L 51/5012* (2013.01); *H01L 51/5056* (2013.01); *H01L 51/5072* (2013.01)

(58) Field of Classification Search
CPC ..... H01L 51/42; H01L 51/50; H01L 51/5012; H01L 51/5056; H01L 51/5072; C07C 49/788; C07C 15/24; C07C 15/38
See application file for complete search history.

(56) References Cited

U.S. PATENT DOCUMENTS

| 9,461,272 | B2 | 10/2016 | Yang |
| 2013/0089724 | A1 | 4/2013 | Poncelet et al. |
| 2017/0288146 | A1 | 10/2017 | Kuwabara et al. |

FOREIGN PATENT DOCUMENTS

| JP | 2004-102223 A | 4/2004 |
| KR | 10-1030012 B1 | 4/2011 |
| KR | 10-2012-0057503 A | 6/2012 |
| KR | 10-2016-0081105 A | 7/2016 |
| KR | 10-1679815 B1 | 11/2016 |
| KR | 10-1981294 B1 | 5/2019 |
| KR | 10-2103589 B1 | 4/2020 |
| WO | WO 2010/038252 A2 | 4/2010 |

OTHER PUBLICATIONS

Fan, Jinming et al.; "Synthesis of Benzoaryl-5-yl(2-hydroxyphenyl)methanones via Photoinduced Rearrangement of (E)-3-Arylvinyl-4H-chromen-4-ones"; Org. Lett.; 19; 2017; pp. 5984-5987.
Extended European Search Report for corresponding European Application No. 18203685.5, dated Mar. 20, 2019, 7 pages.

\* cited by examiner

LIGHT ABSORBER AND ORGANIC ELECTROLUMINESCENCE DEVICE INCLUDING THE SAME

CROSS-REFERENCE TO RELATED APPLICATION

This application claims priority to and the benefit of Korean Patent Application Nos. 10-2017-0144168, filed on Oct. 31, 2017, and 10-2018-0026152, filed on Mar. 6, 2018, the entire content of each of which is hereby incorporated by reference.

BACKGROUND

The present disclosure herein relates to a light absorber and an organic electroluminescence device including the same.

As an image display device, an organic electroluminescence device using an organic electroluminescence device has been actively developed. An organic electroluminescence device is different from a liquid crystal display, and the like, in that it is a so-called self-luminescence display which realizes a display image by recombining holes and electrons injected from a first electrode and a second electrode, respectively, in a light emitting layer to emit light from a light emitting material which is an organic compound included in the light emitting layer.

As an organic electroluminescence device, for example, an organic device may include a first electrode, a hole transport region provided on the first electrode, a light emitting layer provided on the hole transport region, an electron transport region provided on the light emitting layer, and a second electrode provided on the electron transport region. From the first electrode, a hole is injected, and the injected hole moves through the hole transport region to be injected to the light emitting layer. From the second electrode, an electron is injected, and the injected electron moves through the electron transport region to be injected to the light emitting layer. The hole and the electron both injected to the light emitting layer are recombined to generate an exciton in the light emitting layer. An organic electroluminescence device emits light using the light generated when the exciton falls (e.g., transitions or relaxes) back to a ground state. In addition, an organic electroluminescence device is not limited to the configurations described herein and various modifications thereof are possible.

Certain organic electroluminescence devices may be easily deteriorated by being exposed to ultraviolet light in the manufacturing process thereof, or by being exposed to sunlight due to outdoor use. Accordingly, a technology for preventing ultraviolet light and a part of visible light from entering into an organic electroluminescence device has been continuously required.

SUMMARY

The present disclosure provides a light absorber, and an organic electroluminescence device including the same, and for example, a light absorber which efficiently absorbs a part of visible light and ultraviolet light, and a layer including the same.

An embodiment of the present disclosure provides a light absorber represented by Formula 1 below.

$$X-Ar-Y \quad \text{Formula 1}$$

In Formula 1, Ar is pyrene, chrysene, or anthracene, Y is a hydrogen atom, a substituted or unsubstituted alkyl group having 1 to 20 carbon atoms, a substituted or unsubstituted alkenyl group having 2 to 20 carbon atoms, a substituted or unsubstituted alkoxy group having 1 to 20 carbon atoms, a substituted or unsubstituted acrylate group having 1 to 20 carbon atoms, a substituted or unsubstituted aryl group having 6 to 30 ring-forming carbon atoms, a substituted or unsubstituted heteroaryl group having 2 to 30 ring-forming carbon atoms, a substituted or unsubstituted carbonyl group, a substituted or unsubstituted benzophenone group, a substituted or unsubstituted benzoate group, or a substituted or unsubstituted salicylate, and X is represented by any one of Formula 2-1 to 2-3 below.

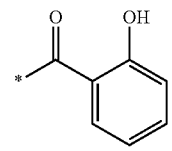

Formula 2-1

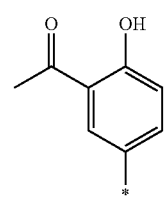

Formula 2-2

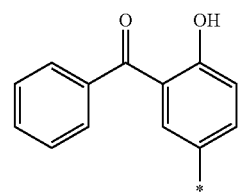

Formula 2-3

In an embodiment, Formula 1 may be represented by any one of Formula 1-1 to 1-3 below.

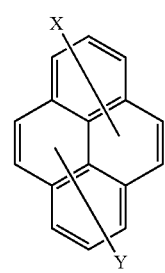

Formula 1-1

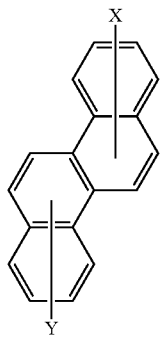

Formula 1-2

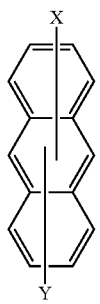

Formula 1-3

In Formula 1-1 to 1-3, X and Y are the same as described above.

In an embodiment, Formula 1 may be represented by any one of Formula 1-4 to 1-6 below.

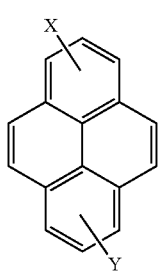

Formula 1-4

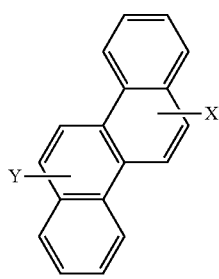

Formula 1-5

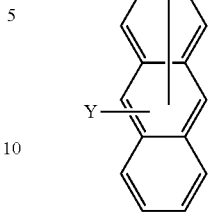

Formula 1-6

In Formula 1-4 to 1-6, X and Y are the same as described above.

In an embodiment, Formula 1 may be represented by any one of Formula 1-7 to 1-9 below.

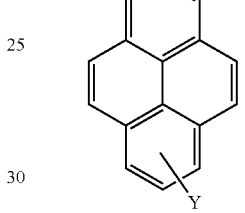

[Formula 1-7]

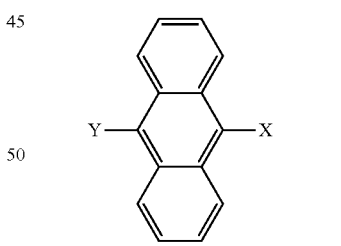

[Formula 1-8]

[Formula 1-9]

In Formula 1-7 to 1-9, X and Y are the same as described above.

In an embodiment, the Y may be a substituted or unsubstituted phenyl group, a substituted or unsubstituted biphenyl group, a substituted or unsubstituted naphthyl group, a substituted or unsubstituted anthracene group, a substituted or unsubstituted phenanthrene group, a substituted or unsubstituted dibenzofuran group, or a substituted or unsubstituted dibenzothiophene group.

In an embodiment, the Y may be represented by any one of the following structural formulas.

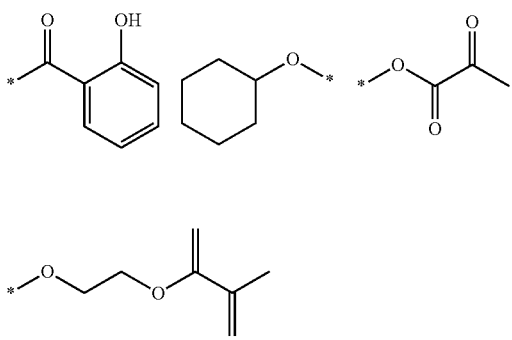

X may be represented by Formula 2-1, and Y may be represented by Formula 3 below.

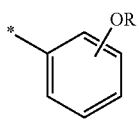

Formula 3

In Formula 3, R is a substituted or unsubstituted alkyl group having 1 to 5 carbon atoms.

In an embodiment, the light absorber may have a degree of light absorbance of 0.7 or more in a wavelength range of 380 nm to 410 nm.

In an embodiment of the present disclosure, an organic electroluminescence device includes a hole transport region provided on a first electrode, a light emitting layer provided on the hole transport region, an electron transport region provided on the light emitting layer, a second electrode provided on the electron transport region, and a light absorbing layer provided on at least one of a lower portion of the first electrode and an upper portion of the second electrode, wherein the light absorbing layer includes a light absorber according to an embodiment of the present disclosure.

In an embodiment, the light absorbing layer may be disposed on the second electrode, and may be in contact with the second electrode.

In an embodiment, the light absorbing layer may be a thin film encapsulating layer covering the first electrode, the hole transport region, the light emitting layer, the electron transport region, and the second electrode.

In an embodiment of the present disclosure, an organic electroluminescence device includes a hole transport region provided on a first electrode, a light emitting layer provided on the hole transport region, an electron transport region provided on the light emitting layer, a second electrode provided on the electron transport region, and a light absorbing layer provided on at least one of a lower portion of the first electrode and an upper portion of the second electrode, wherein the light absorbing layer includes a light absorber including a polycyclic aromatic compound, and the polycyclic aromatic compound is substituted with a substituent including a structure represented by Formula A below.

Formula A

In Formula A above, are each independently a position substituted with the polycyclic aromatic compound or a position substituted with a hydrogen atom or a substituted or unsubstituted aryl group having 6 to 30 ring-forming carbon atoms.

In an embodiment, the polycyclic aromatic compound may include pyrene, chrysene, or anthracene.

In an embodiment, the polycyclic aromatic compound may further be substituted with a substituted or unsubstituted alkyl group having 1 to 20 carbon atoms, a substituted or unsubstituted alkenyl group having 2 to 20 carbon atoms, a substituted or unsubstituted alkoxy group having 1 to 20 carbon atoms, a substituted or unsubstituted acrylate group having 1 to 20 carbon atoms, a substituted or unsubstituted aryl group having 6 to 30 ring-forming carbon atoms, a substituted or unsubstituted heteroaryl group having 2 to 30 ring-forming carbon atoms, a substituted or unsubstituted carbonyl group, a substituted or unsubstituted benzophenone group, a substituted or unsubstituted benzoate group, or a substituted or unsubstituted salicylate.

In an embodiment, the polycyclic aromatic compound may further be substituted with a substituent represented by Formula 3 below.

Formula 3

In Formula 3, R is a substituted or unsubstituted alkyl group having 1 to 5 carbon atoms.

BRIEF DESCRIPTION OF THE FIGURES

The accompanying drawings are included to provide a further understanding of embodiments of the present disclosure, and are incorporated in and constitute a part of this specification. The drawings illustrate exemplary embodiments of the present disclosure and, together with the description, serve to explain principles of the present disclosure. In the drawings.

DETAILED DESCRIPTION

Figure 1:
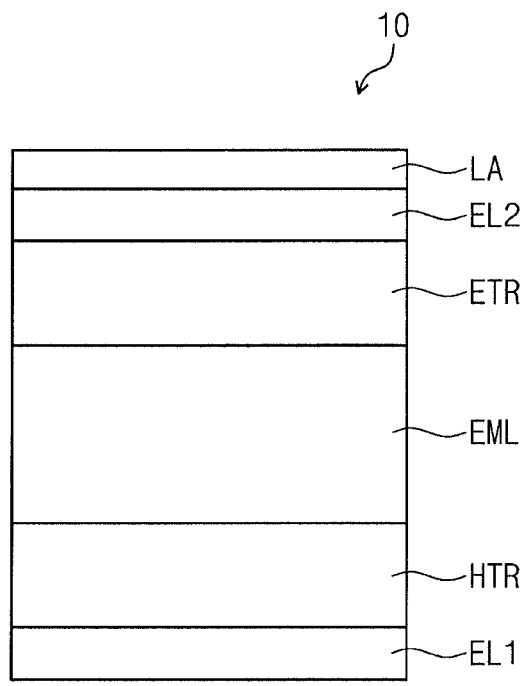
FIG. 1 is a cross-sectional view schematically showing an organic electroluminescence device according to an embodiment of the present disclosure.

Features of the subject matter of the present disclosure may be understood easily by reference to the exemplary embodiments and the accompanying drawings. The subject matter of the present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art.

In describing each drawing, similar reference numerals were used for similar elements. Also, in the accompanying drawings, the dimensions of structures may be exaggerated for clarity of the present disclosure. It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present disclosure. The terms of a singular form may include plural forms unless the context clearly indicates otherwise.

In this application, the terms "comprise" or "have," and the like, are intended to designate features, numbers, steps, operations, elements, parts, or combinations thereof described in the specification of the present disclosure but not to exclude the possibility of the presence or the addition of one or more other features, numbers, steps, operations, elements, parts, or combinations thereof. It will also be understood that when a portion, such as a layer, a film, a region, and a plate is referred to as being "on" another portion, it can be "directly on" the other portion, or one or more intervening portions may also be present. On the other hand, it will be understood that when a portion, such as a layer, a film, a region, and a plate is referred to as being "under" another portion, it can be "directly under", or one or more intervening portions may also be present.

In this application, "substituted or unsubstituted" may mean being substituted or unsubstituted with one or more substituents selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl groups, and a heterocyclic group. In addition, each of the substituents illustrated above may be substituted or unsubstituted. For example, a biphenyl group may be interpreted as an aryl group, and may be interpreted as a phenyl group substituted with a phenyl group.

In this application, examples of a halogen atom may include a fluorine atom, a chlorine atom, a bromine atom, or an iodine atom.

In this application, an alkyl group may be linear, branched or cyclic. The number of carbon atoms of the alkyl group may be 1 to 30, 1 to 20, 1 to 10, 1 to 6, or any range subsumed therein. Examples of the alkyl group may include a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantly group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldodecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-heneicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, and an n-triacontyl group, and the like, but are not limited thereto.

In this application, an alkenyl group may be linear or branched. The number of carbon atoms is not particularly limited, but may be 2 to 30, 2 to 20, 2 to 10, or any range subsumed therein. Examples of the alkenyl group may include, a vinyl group, a 1-butenyl group, a 1-pentenyl group, a 1,3-butadienylaryl group, a styrenyl group, a styryl vinyl group, and the like, but are not limited thereto.

In this application, an aryl group may be any functional group or substituent derived from an aromatic hydrocarbon ring. The aryl group may be a monocyclic aryl group or a polycyclic aryl group. The number of ring-forming carbon atoms of the aryl group may be 6 to 60, 6 to 30, 6 to 20, 6 to 15, or any range subsumed therein. Examples of the aryl group may include a phenyl group, a naphthyl group, a fluorenyl group, an anthracenyl group, a phenanthryl group, a biphenyl group, a terphenyl group, a quaterphenyl group, a quinphenyl group, a sexiphenyl group, a biphenylene group, a triphenylene group, a pyrenyl group, a benzofluoranthenyl group, a chrysenyl group, and the like, but are not limited thereto.

In this application, the fluorenyl group may be substituted, and two substituents may be bonded to each other to form a Spiro structure. Examples of the case in which a fluorenyl group is substituted are as follows. However, the embodiment of the present disclosure is not limited thereto.

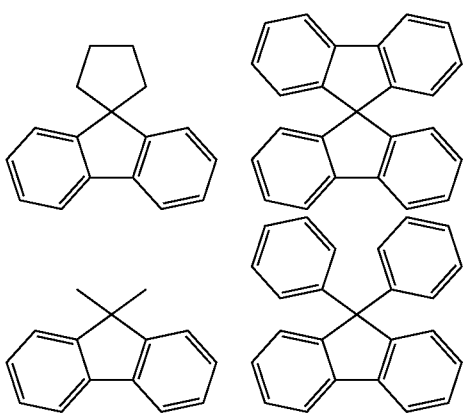

In this application, a heteroaryl group may be a heteroaryl group including one or more of O, N, P, Si or S as a heteroatom. When the heteroaryl group includes two heteroatoms, the two heteroatoms may be the same or different. The number of ring-forming carbon atoms of the heteroaryl group may be 2 to 60, 2 to 30, 2 to 20, or any range subsumed therein. The heteroaryl group may be a monocyclic heteroaryl group or a polycyclic heteroaryl group. The polycyclic heteroaryl group may be, for example, one having a bicyclic or tricyclic structure. Examples of the heteroaryl group may include a thiophene group, a furan group, a pyrrole group, an imidazole group, a thiazole group, an oxazole group, an oxadiazole group, a triazole group, a pyridine group, a bipyridine group, a pyrimidine group, a triazine group, a triazole group, an acridyl group, a pyridazine group, a pyrazinyl group, a quinolinyl group, a quinazoline group, a quinoxalinyl group, a phenoxazine group, a phthalazine group, a pyridopyrimidine group, a pyridopyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophene group, a thienothiophenyl group, a benzofuran group, a phenanthroline group, a thiazole group, an isoxazole group, an oxadiazole group, a thiadiazole group, a phenothiazine, a dibenzosilyl group, a dibenzofuran group, and the like, but are not limited thereto.

In this application, a silyl group includes an alkylsilyl group and an arylsilyl group. Examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In this application, a boron group includes an alkyl boron group and an aryl boron group. Examples of the boron group may include a trimethylboron group, a triethylboron group, a t-butyldimethylboron group, a triphenylboron group, a diphenylboron group, a phenylboron group, and the like, but are not limited thereto.

In this application, the number of carbon atoms of the amino group is not particularly limited, but may be 1 to 30, or any range subsumed therein. The amino group may include an alkylamino group and an arylamino group. Examples of the amino group may include a methylamino group, a dimethylamino group, a phenylamino group, a diphenylamino group, a naphthylamino group, a 9-methylanthracenylamino group, a triphenylamino group, and the like, but are not limited to.

In this application, a phosphine oxide group may be substituted with, for example, at least one of an alkyl group and an aryl group. Examples of the phosphine oxide group may include a phenylphosphine oxide group, a diphenylphosphine oxide group, and the like, but are not limited thereto.

In this application, the number of carbon atoms of the carbonyl group is not particularly limited, but may be, for example, 1 to 30, or any range subsumed therein.

In this application, an alkoxy group may be linear, branched or cyclic. The number of carbon atoms of the alkoxy group may be 1 to 30, 1 to 20, 1 to 10, or any range subsumed therein. Examples of the alkoxy group may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, cyclohexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In this application, the number of carbon atoms of the acrylate may be 1 to 20, 1 to 10, or any range subsumed therein. The alkyl moiety of the acrylate may be a substituted or unsubstituted alkyl group or a cycloalkyl group.

First, a light absorber according to an embodiment of the present disclosure will be described.

The light absorber according to an embodiment of the present disclosure is represented by Formula 1 below.

X—Ar—Y              Formula 1

In Formula 1, Ar is pyrene, chrysene, or anthracene.

In Formula 1, Y is a hydrogen atom, a substituted or unsubstituted alkyl group having 1 to 20 carbon atoms, a substituted or unsubstituted alkenyl group having 2 to 20 carbon atoms, a substituted or unsubstituted alkoxy group having 1 to 20 carbon atoms, a substituted or unsubstituted acrylate group having 1 to 20 carbon atoms, a substituted or unsubstituted aryl group having 6 to 30 ring-forming carbon atoms, a substituted or unsubstituted heteroaryl group having 2 to 30 ring-forming carbon atoms, a substituted or unsubstituted carbonyl group, a substituted or unsubstituted benzophenone group, a substituted or unsubstituted benzoate group, or a substituted or unsubstituted salicylate.

In Formula 1, X is represented by any one of Formulas 2-1 to 2-3 below.

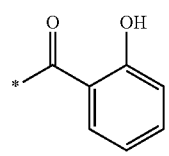

Formula 2-1

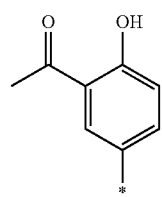

Formula 2-2

-continued

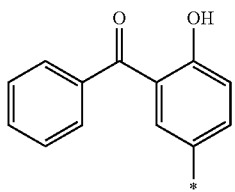

Formula 2-3

In Formula 2-1 to 2-3, -* means a portion to be connected to Ar of Formula 1.

Formula 1 may be, for example, represented by any one of Formulas 1-1 to 1-3 below.

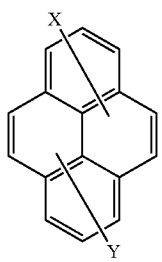

Formula 1-1

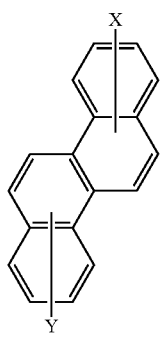

Formula 1-2

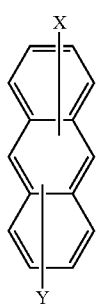

Formula 1-3

In Formula 1-1 to 1-3, X and Y are the same as defined above.

Formula 1-1 may be, for example, represented by Formula 1-4 below, Formula 1-2 may be represented by Formula 1-5 below, and Formula 1-3 may be represented by Formula 1-6 below.

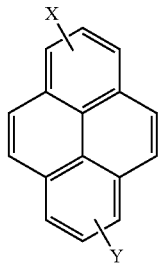

Formula 1-4

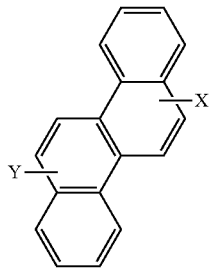

Formula 1-5

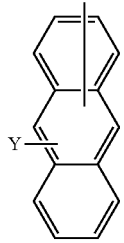

Formula 1-6

In Formula 1-4 to 1-6, X and Y are the same as defined above.

Formula 1-1 may be, for example, represented by Formula 1-7 below, Formula 1-2 may be represented by Formula 1-8 below, and Formula 1-3 may be represented by Formula 1-9 below. However, the substitution position of X and Y is not limited thereto.

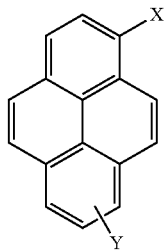

Formula 1-7

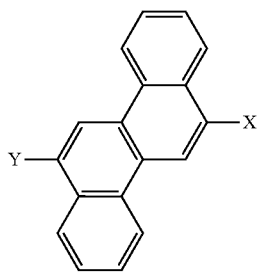

Formula 1-8

-continued

Formula 1-9

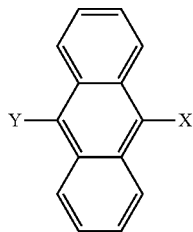

In Formula 1-7 to 1-9 above, X and Y are the same as defined above.

Formula 1-7 may be represented by any one of Formulas 1-10 to 1-12 below.

Formula 1-10

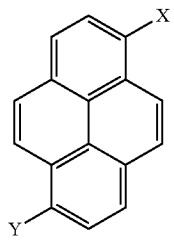

Formula 1-11

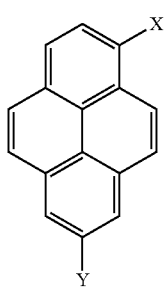

Formula 1-12

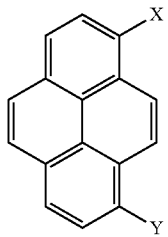

In Formula 1-10 to 1-12 above, X and Y are the same as defined above.

The embodiment of the present disclosure is not limited thereto, however, in Formula 1, Ar may be pyrene.

In Formula 1, Y may be a substituted or unsubstituted aryl group having 6 to 15 ring-forming carbon atoms, a substituted, or unsubstituted polycyclic heteroaryl group.

In Formula 1, Y may be a substituted or unsubstituted phenyl group, a substituted or unsubstituted biphenyl group, a substituted or unsubstituted naphthyl group, a substituted or unsubstituted anthracene group, a substituted or unsubstituted phenanthrene group, a substituted or unsubstituted dibenzofuran group, or a substituted or unsubstituted dibenzothiophene group.

In Formula 1, Y may be a substituted or unsubstituted phenyl group, a substituted or unsubstituted biphenyl group, and when a phenyl group and a biphenyl group are substituted, a substituent may be an alkoxy group having 1 to 10 carbon atoms.

In Formula 1, Y may be represented by Formula 3 below.

Formula 3

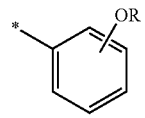

In Formula 3, R is a substituted or unsubstituted alkyl group having 1 to 5 carbon atoms. For example, R may be a substituted or unsubstituted methyl group.

Formula 3 may be represented by Formula 3-1 or Formula 3-2 below.

Formula 3-1

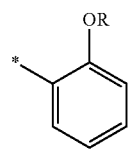

Formula 3-2

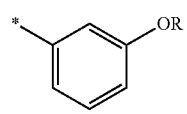

In Formula 3-1 and Formula 3-2, R is the same as described above.

However, the embodiment of the present disclosure is not limited thereto. X may be represented by Formula 2-1, and Y may be represented by Formula 3.

Formula 1 may be, for example, represented by Formula 1-13 below.

Formula 1-13

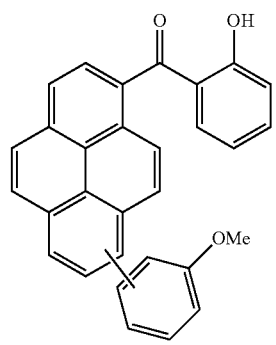

In Formula 1, Y may be represented by any one of the following structural formulas.

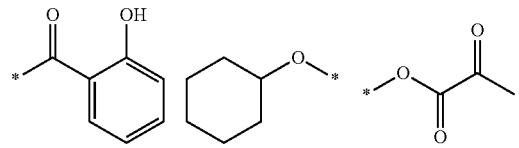

-continued

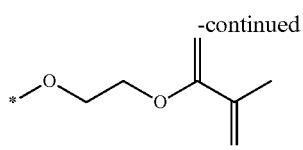

5

In the structural formulas above, -* means a portion to be connected to Ar of Formula 1.

The light absorber represented by Formula 1 may have a maximum absorption wavelength in ultraviolet light (e.g., in an ultraviolet light wavelength range) and in a part of visible light (e.g., in a visible light wavelength range). For example, the light absorber represented by Formula 1 may have a maximum absorption wavelength of 380 nm to 410 nm. For example, the light absorber represented by Formula 1 may have a degree of light absorbance of 0.7 or more in a wavelength range of 380 nm to 410 nm. Although not limited thereto, the light absorber represented by Formula 1 may have a degree of light absorbance of 0.8 or more, or 0.85 or more in a wavelength range of 380 nm to 410 nm.

The light absorber represented by Formula 1 according to an embodiment of the present disclosure may be any one selected from the compounds represented by Compound group 1 below, however, is not limited thereto.

Compound group 1

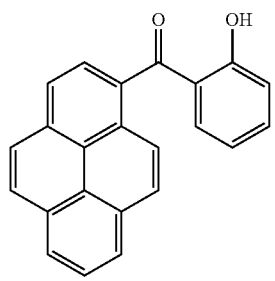

1

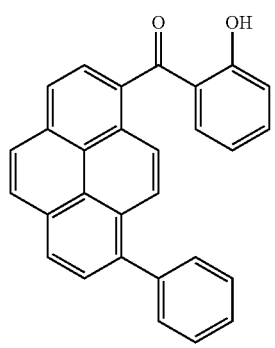

2

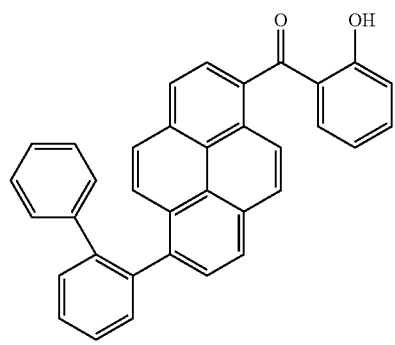

3

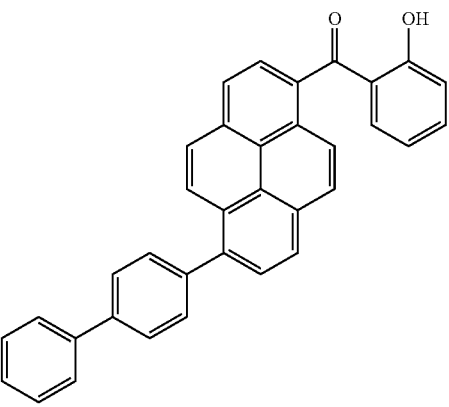

4

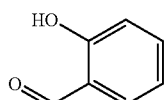

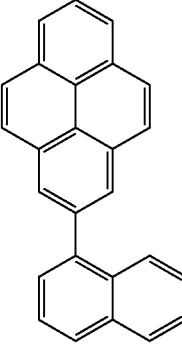

5

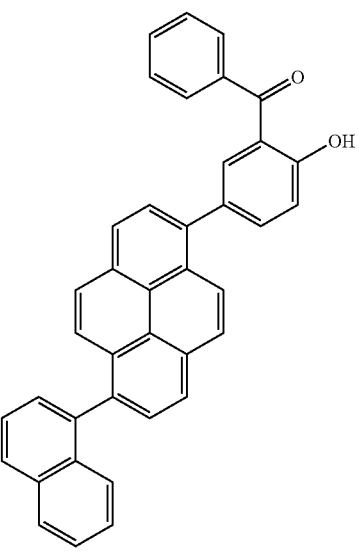

6

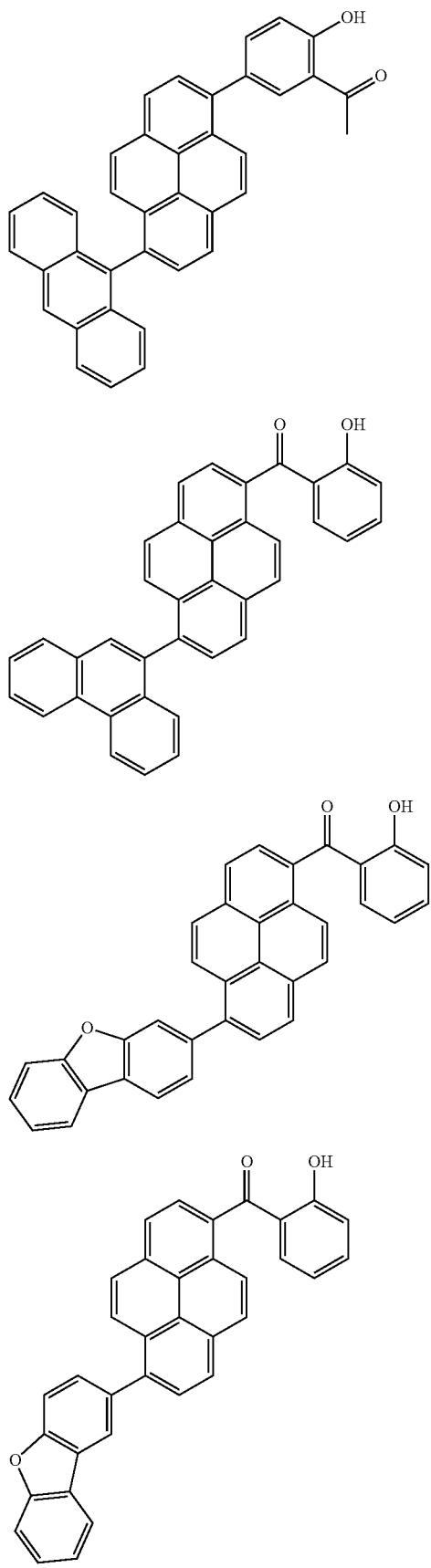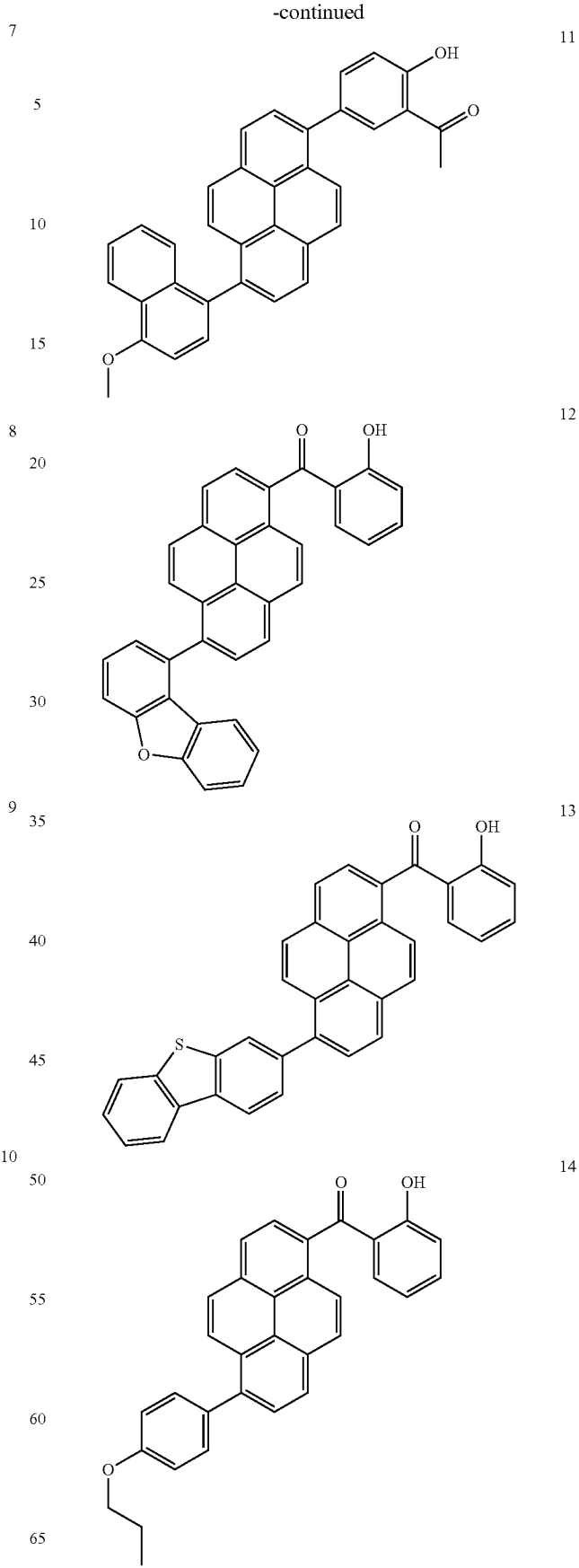

-continued
15
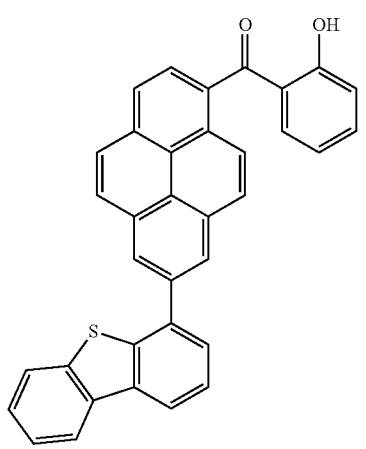
16
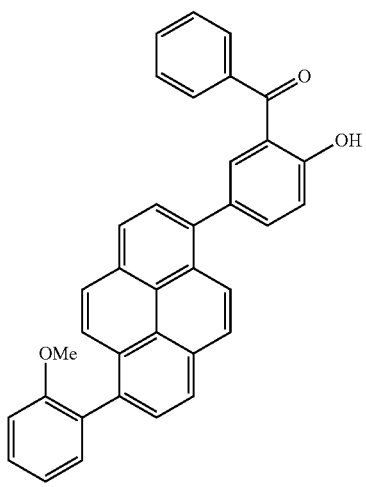
17
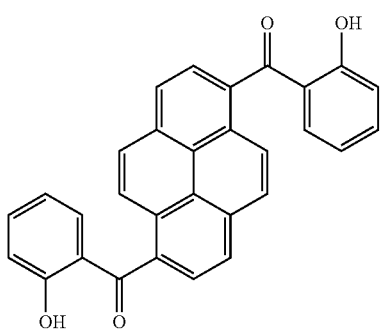
18
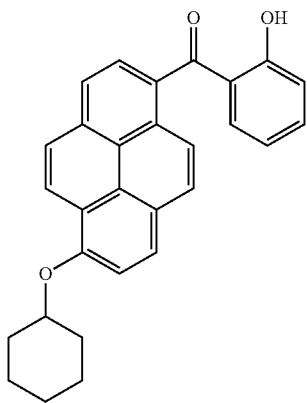
-continued
19
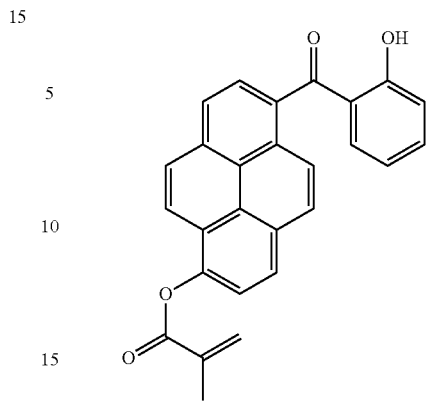
20
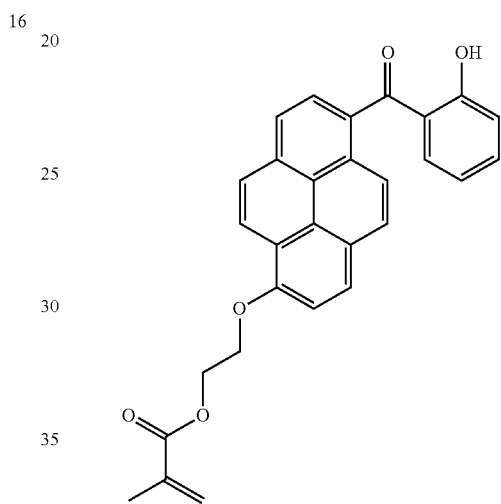
21
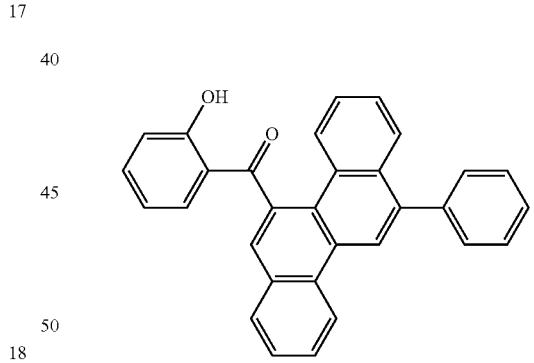
22
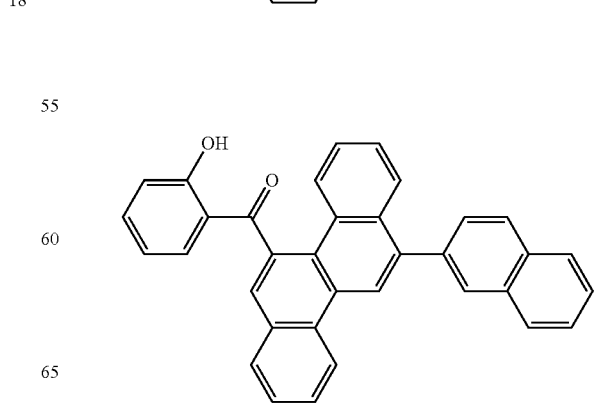

23
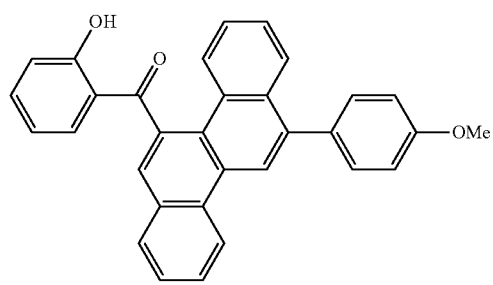
24
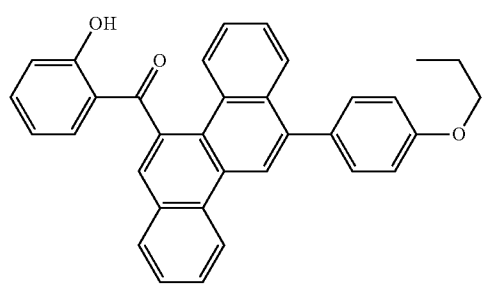
25
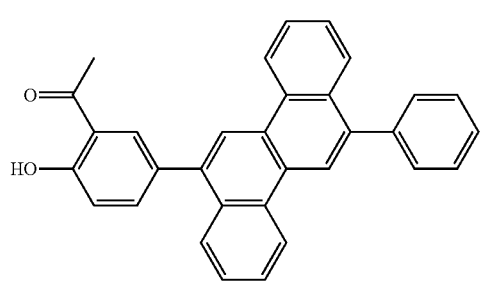
26
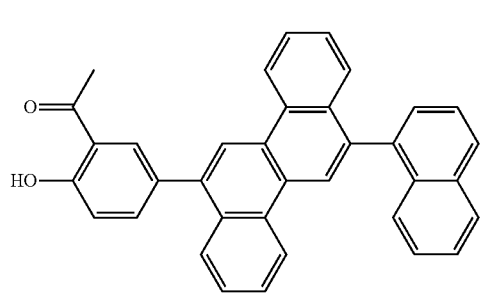
27
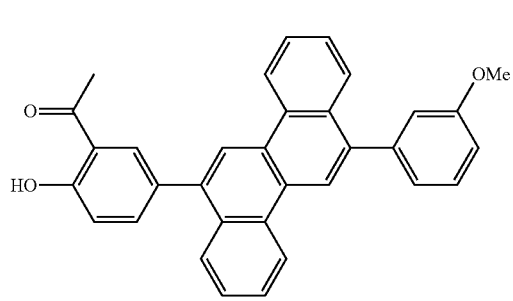
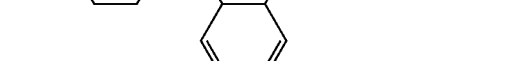
28
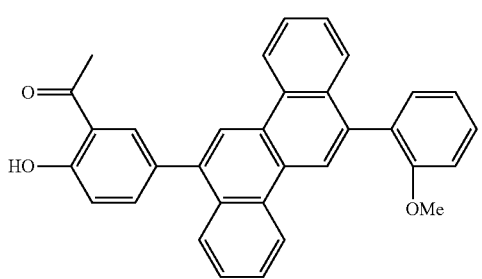
29
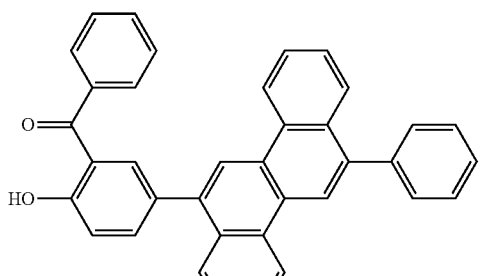
30
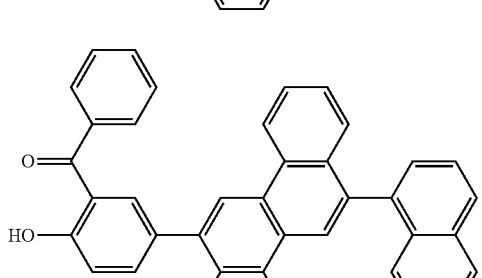
31
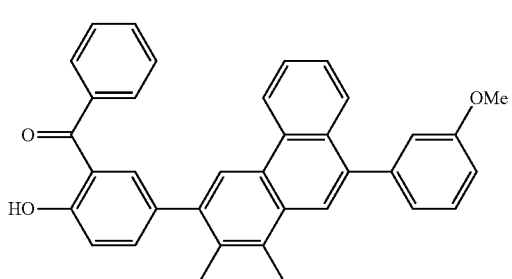
32
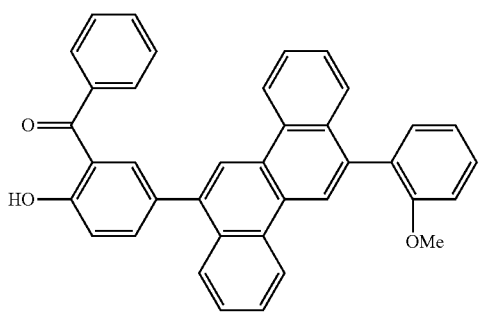

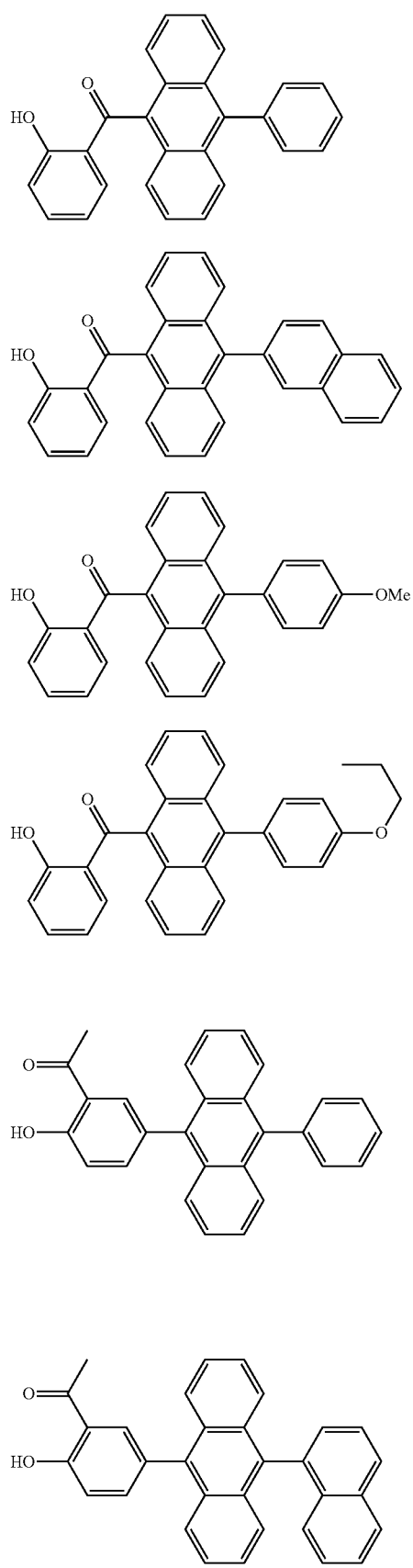
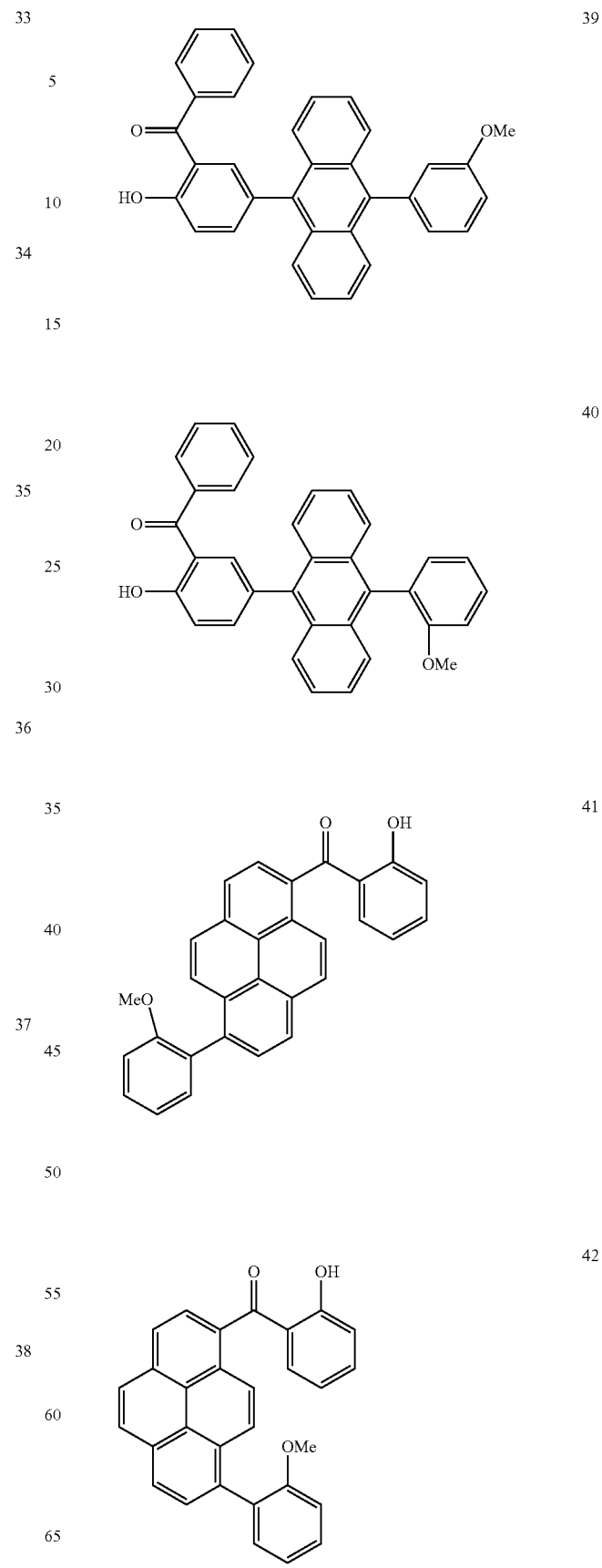

-continued

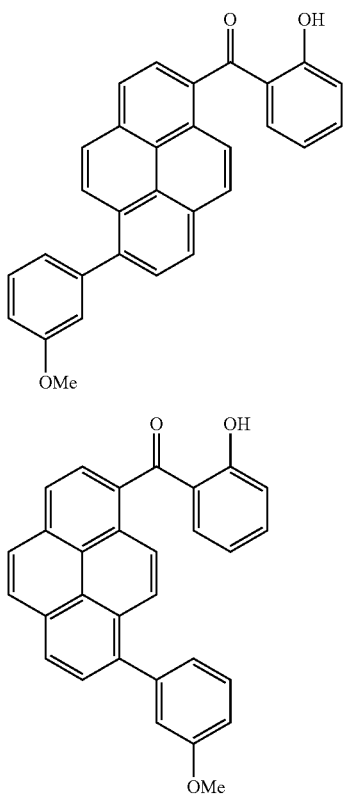

43

44

The light absorber according to an embodiment of the present disclosure efficiently absorbs ultraviolet light and a part of visible light, and for example, has a maximum absorption wavelength of 380 nm to 410 nm. For example, the light absorber according to an embodiment of the present disclosure may have a light absorbance of 0.7 or more, or 0.8 or more in a wavelength range of 380 nm to 410 nm, and accordingly, may appropriately be utilized where blocking of ultraviolet light and a part of visible light is required. For example, the light absorber according to an embodiment of the present disclosure may be utilized for an organic electroluminescence device, and may prevent, minimize, or reduce the deterioration of an organic layer, such as a light emitting layer in the organic electroluminescence device due to ultraviolet light or a part of visible light.

The light absorber represented by Formula 1 may be produced based on a synthesis example described herein below. However, a process of synthesizing the light absorber represented by Formula 1 is not limited to the synthesis example described herein. Any reaction condition may be used if reaction condition is generally used in the art.

Hereinafter, an organic electroluminescence device according to an embodiment of the present disclosure will be described. Hereinafter, differences from the light absorber according to an embodiment of the present disclosure will be described in more detail. Parts that are not described below correspond to the light absorber according to an embodiment of the present disclosure.

An organic electroluminescence device according to an embodiment of the present disclosure includes the light absorber according to an embodiment of the present disclosure.

Figure 2:
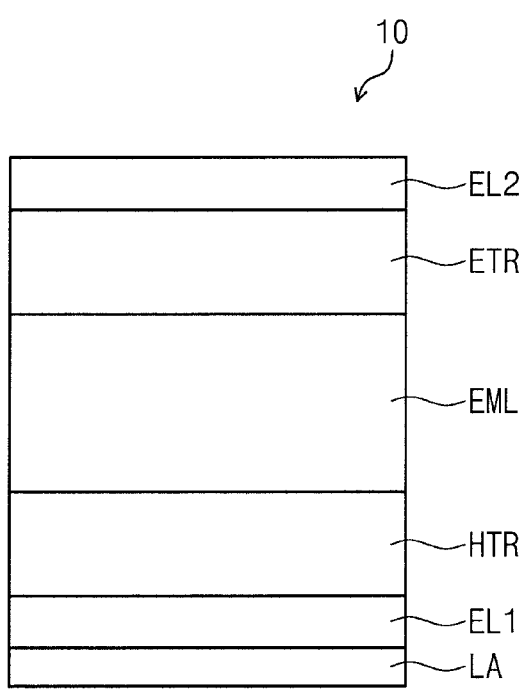
FIG. 2 is a cross-sectional view schematically showing an organic electroluminescence device according to an embodiment of the present disclosure.
Figure 3:
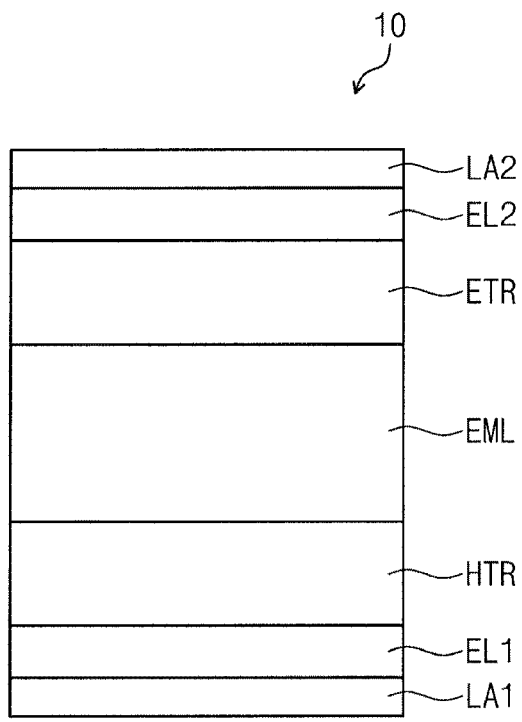
FIG. 3 is a cross-sectional view schematically showing an organic electroluminescence device according to an embodiment of the present disclosure.
Figure 4:
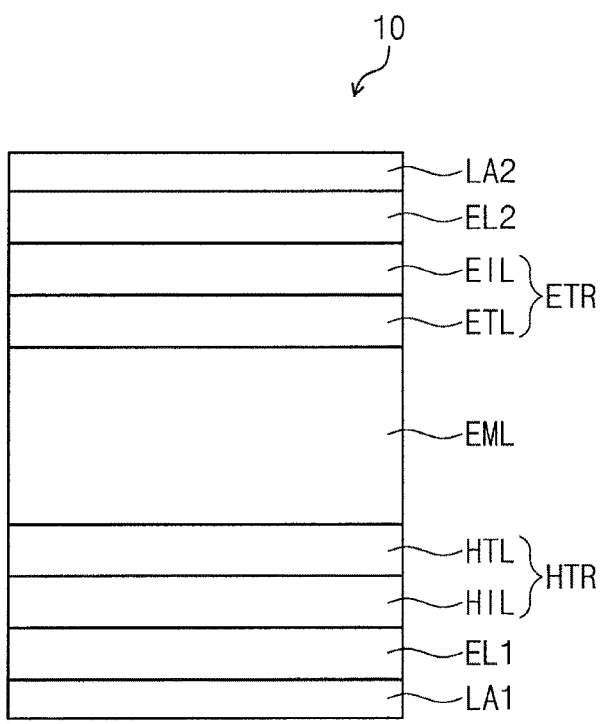
FIG. 4 is a cross-sectional view schematically showing an organic electroluminescence device according to an embodiment of the present disclosure.
Figure 5:
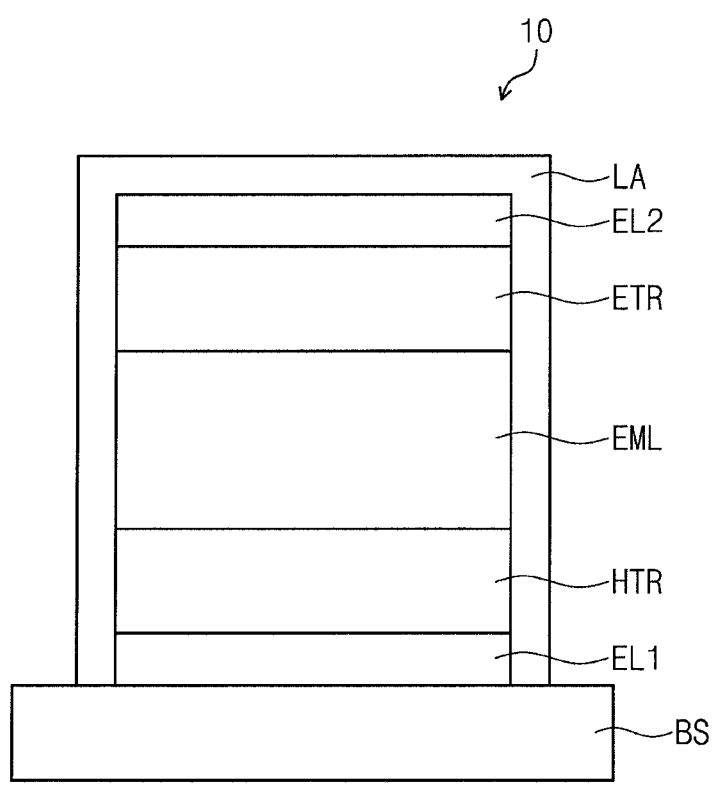
FIG. 5 is a cross-sectional view schematically showing an organic electroluminescence device according to an embodiment of the present disclosure.

FIG. 1 is a cross-sectional view schematically showing an organic electroluminescence device according to an embodiment of the present disclosure. FIG. 2 is a cross-sectional view schematically showing an organic electroluminescence device according to an embodiment of the present disclosure. FIG. 3 is a cross-sectional view schematically showing an organic electroluminescence device according to an embodiment of the present disclosure. FIG. 4 is a cross-sectional view schematically showing an organic electroluminescence device according to an embodiment of the present disclosure. FIG. 5 is a cross-sectional view schematically showing an organic electroluminescence device according to an embodiment of the present disclosure.

Referring to FIGS. 1-4, an organic electroluminescence device 10 according to an embodiment of the present disclosure includes a first electrode EL1, a hole transport region HTR, a light emitting layer EML, an electron transport region ETR, a second electrode EL2, and a light absorbing layer LA. The light absorbing layer LA includes a light absorber according to an embodiment of the present disclosure. For example, the light absorbing layer LA includes a light absorber represented by Formula 1 below.

   Formula 1

In Formula 1, the detailed description of X, Ar, and Y is the same as described above.

The light absorbing layer LA may include one, or two or more kinds of light absorbers according to an embodiment of the present disclosure. The light absorber according to an embodiment of the present disclosure may have a maximum absorption wavelength in ultraviolet light (e.g., in an ultraviolet light wavelength range) and in a part of visible light (e.g., in a visible light wavelength range), for example, a maximum absorption wavelength of 380 nm to 410 nm, and for example, may have a degree of light absorbance of 0.7 or more in a wavelength range of 380 nm to 410 nm.

The first electrode EL1 and the second electrode EL2 are disposed to face each other, and between the first electrode EL1 and the second electrode EL2, a plurality of organic layers may be disposed. The plurality of organic layers may include the hole transport region HTR, the light emitting layer EML, and the electron transport region ETR.

The light absorbing layer LA is provided on at least one of a lower portion of the first electrode EL1 or an upper portion of the second electrode EL2. FIG. 1 illustrates the light absorbing layer LA provided on an upper portion of the first electrode EL1, and FIG. 2 illustrates the light absorbing layer LA provided on a lower portion of the second electrode EL2. FIGS. 3-4 each illustrates the light absorbing layer LA provided on a lower portion of the first electrode EL1, and on an upper portion of the second electrode EL2. In this case, the light absorbing layer LA may include a first light absorbing layer LA1 provided on a lower portion of the first electrode EL1, and a second light absorbing layer LA2 provided on an upper portion of the second electrode EL2.

The light absorber according to an embodiment of the present disclosure may be included in other components other than the light absorbing layer LA if necessary. Furthermore, the light absorbing layer LA may further include any suitable light absorber available in the art together with the light absorber according to an embodiment of the present disclosure.

FIG. 5 is a cross-sectional view schematically showing an organic electroluminescence device according to an embodiment of the present disclosure.

Referring to FIG. 5, the light absorbing layer LA may be a thin film encapsulating layer covering the first electrode EL1, the hole transport region HTR, the light emitting layer EML, the electron transport region ETR, and the second electrode EL2. The organic electroluminescence device 10 according to an embodiment of the present disclosure may further include a base substrate BS. On one surface of the base substrate BS, the first electrode EL1, the hold transport region HTR, the light emitting layer EML, the electron transport region ETR, and the second electrode EL2 may be sequentially provided. The thin film encapsulating layer encapsulates the first electrode EL1, the hold transport region HTR, the light emitting layer EML, the electron transport region ETR, and the second electrode EL2 along with the base substrate BS to prevent oxygen and moisture from penetrating into the light emitting layer EML and the like (or to reduce a likelihood or amount of oxygen and moisture from penetrating into the light emitting layer EML and the like), and in the case in which the thin film encapsulating layer is the light absorbing layer LA, the thin film encapsulating layer also prevents or reduces the penetration of ultraviolet light and a part of visible light. The thin film encapsulating layer may have a multilayer structure in which one or more inorganic layers and one or more organic layers are alternately laminated thereon, and at least one of the organic layers may include the light absorber represented by Formula 1 described above. The organic layer of the thin film encapsulating layer may further include any suitable light absorber available in the art other than the light absorber represented by Formula 1 described above. The inorganic layer may include any suitable material known in the art, for example, at least one selected from silicon nitride, silicon oxynitride, titanium oxide, aluminum oxide, and silicon oxide.

However, the embodiment of the present disclosure is not limited thereto. For example, the light absorbing layer LA may be a capping layer provided on the second electrode EL2. The capping layer may further include a material known in the art other than the light absorber according to an embodiment of the present disclosure, for example, α-NPD, NPB, TPD, m-MTDATA, Alq3, CuPc, TPD15 (N4,N4,N4',N4'-tetra (biphenyl-4-yl) biphenyl-4,4'-diamine), TCTA (4,4',4"-Tris (carbazol sol-9-yl) triphenylamine), N,N'-bis (naphthalen-1-yl), and the like. The capping layer serves to efficiently emit light emitted from the light emitting layer EML to the outside of the organic electroluminescence device.

When the organic electroluminescence device 10 according to an embodiment of the present disclosure includes both a capping layer and a thin film encapsulating layer, the capping layer may be provided between the second electrode EL2 and the thin film encapsulating layer, and at least one of the capping layer and the thin film encapsulating layer may include the light absorber according to an embodiment of the present disclosure.

When the light absorbing layer LA is provided on a lower portion of the first electrode EL1, the light absorbing layer LA may be provided between the first electrode EL1 and the base substrate BS.

The thicknesses of the light absorbing layer LA may be, for example, about 500 Å to about 1000 Å, but is not limited thereto, and the thickness may be adjusted if necessary.

The light absorbing layer LA may further include other components other than the light absorber according to an embodiment of the present disclosure, for example, an antioxidant, a binder, and the like, but is not limited thereto.

The light absorbing layer LA may be provided by various suitable methods such as vacuum deposition, spin coating, casting, Langmuir-Blodgett (LB), inkjet printing, laser printing, and laser induced thermal imaging (LITI).

Hereinafter, referring to FIGS. 1-4 again, each layer will be described in more detail.

The first electrode EL1 has conductivity. The first electrode EL1 may be a pixel electrode or a positive electrode. The first electrode EL1 may be a transmissive electrode, a transflective electrode, or a reflective electrode. When the first electrode EL1 is a transmissive electrode, the first electrode EL1 may include a transparent metal oxide, for example, indium tin oxide (ITO), indium zinc oxide (IZO), zinc oxide (ZnO), indium tin zinc oxide (ITZO), and the like. When the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, or a compound or a mixture thereof (for example, a mixture of Ag and Mg). Also, the first electrode EL1 may have a multilayer structure including a reflective film or a transflective film, both formed of the above materials, and a transparent conductive film formed of indium tin oxide (ITO), indium zinc oxide (IZO), zinc oxide (ZnO), indium tin zinc oxide (ITZO), and the like. For example, the first electrode EL1 may have a three-layer structure of ITO/Ag/ITO, but is not limited thereto.

The thicknesses of the first electrode EL1 may be about 1000 Å to about 10000 Å, for example, about 1000 Å to about 3000 Å.

The hole transport region HTR is provided on the first electrode EL1. The hole transport region HTR may include at least one of a hole injection layer HIL, a hole transport layer HTL, a hole buffer layer, or an electron blocking layer. The thickness of the hole transport region HTR may be, for example, about 1000 Å to 1500 Å.

The hole transport region HTR may have a single layer structure having a single layer formed of a single material, a single layer structure having a single layer formed of a plurality of different materials, or a multilayer structure having a plurality of layers formed of a plurality of different materials.

For example, the hole transport region HTR may have a single layer structure having a single layer of the hole injection layer HIL or the hole transport layer HTL, or have a single layer structure having a single layer formed of a hole injection material and a hole transport material. Also, the hole transport region HTR may have a single layer structure having a single layer formed of a plurality of different materials, or have a structure of the hole injection layer HIL/the hole transport layer HTL, the hole injection layer HIL/the hole transport layer HTL/the hole buffer layer, the hole injection layer HIL/the hole buffer layer, the hole transport layer HTL/the hole buffer layer, or the hole injection layer HIL/the hole transport layer HTL/the electron blocking layer, sequentially laminated on the first electrode EL1, but the embodiment of the present disclosure is not limited thereto.

The hole transport region HTR may be provided by various suitable methods such as vacuum deposition, spin coating, casting, Langmuir-Blodgett (LB), inkjet printing, laser printing, and laser induced thermal imaging (LITI).

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino) triphenylamine (m-MTDATA), 4,4'4"-Tris(N,N-diphenylamino)triphenylamine (TDATA), 4,4',4"-tris{N-(2-naphthyl)-N-phenylamino}-triphenylarnine (2-TNATA), Poly(3,4-ethylenedioxythiophene)/Poly (4-styrenesulfonate) (PEDOT/PSS), Polyaniline/Dodecylbenzenesulfonic acid (PANI/DBSA), Polyaniline/Camphor sulfonicacid PANI/CSA), (Polyaniline)/Poly(4-styrene-sulfonate) (PANI/PSS), N,N'-Di[(1-naphthyl)-N,N'-diphenyl]-1,1-(biphenyl)-4,4'-diamine (NPB), a carbazole-based derivative such as N-phenylcarbazole and polyvinylcarbazole, a fluorene-based derivative, triphenylamine-containing polyether ketone (TPAPEK), 4-Isopropyl-4'-methyldiphenyliodonium Tetrakis(pentafluorophenyl)borate], dipyrazino [2,3-f: 2',3'-h] quinoxaline-2,3,6,7,10,11-hexacarbonitrile (HAT-CN), and the like.

The hole transport layer HTL may include, for example, a carbazole-based derivative such as N-phenylcarbazole and polyvinylcarbazole, a fluorine-based derivative, a triphenylamine-based derivative such as N,N'-bis(3-methylphenyl)-N,N'-diphenyl-[1,1-biphenyl]-4,4'-diamine (TPD) and 4,4',4''-tris(N-carbazolyl)triphenylamine (TCTA), N,N-Di (1-naphthyl)-N,N-diphenyl-(1,1-biphenyl)-4,4-diamine (NPB), 4,4'-Cyclohexylidene bis[N,N-bis(4-methylphenyl)benzenamine] (TAPC), 4,4'-Bis[N,N'-(3-tolyl)amino]-3,3'-dimethylbiphenyl (HMTPD), 1,3-Bis(N-carbazolyl)benzene (mCP), and the like.

The thickness of the hole transport region HTR may be about 100 Å to about 10000 Å, for example, about 100 Å to about 1000 Å. When the hole transport region HTR includes both the hole injection layer HIL and the hole transport layer HTL, the thickness of the hole injection layer HIL may be about 100 Å to about 1000 Å, and the thickness of the hole transport layer HTL may be about 30 Å to about 1000 Å. When the thicknesses of the hole transport region HTR, the hole injection layer HIL, and the hole transport layer HTL satisfy the above-described ranges, a suitable or satisfactory hole transport characteristic may be obtained without a substantial increase in driving voltage.

The hole transport region HTR may further include a charge generating material to improve conductivity other than the above-mentioned materials. The charge generating material may be uniformly or non-uniformly dispersed in the hole transport region HTR. The charge generating material may be, for example, a p-dopant. The p-dopant may be one of a quinone derivative, a metal oxide, or a compound containing a cyano group, but is not limited thereto. For example, non-limiting examples of the p-dopant may include a quinone derivative such as tetracyanoquinodimethane (TCNQ) and 2,3,5,6-tetrafluoro-tetracyanoquinodimethane (F4-TCNQ), and a metal oxide such as a tungsten oxide and a molybdenum oxide, but are not limited thereto.

As described above, the hole transport region HTR may further include at least one of the hole buffer layer and the electron blocking layer other than the hole injection layer HIL and the hole transport layer HTL. The hole buffer layer may increase the light emission efficiency by compensating the resonance distance according to the wavelength of light emitted from the light emitting layer EML. As a material to be included in the hole buffer layer, a material which may be included in the hole transport region HTR may be used. The electron blocking layer is a layer which serves to prevent an electron from being injected from the electron transport region ETR to the hole transport region HTR (or to reduce a likelihood or amount of electrons being injected from the electron transport region ETR to the hole transport region HTR).

The light emitting layer EML is provided on the hole transport region HTR. The thickness of the light emitting layer EML may be, for example, about 100 Å to about 1000 Å, or about 100 Å to about 300 Å. The light emitting layer EML may have a single layer structure having a single layer formed of a single material, a single layer structure having a single layer formed of a plurality of different materials, or a multilayer structure having a plurality of layers formed of a plurality of different materials.

The light emitting layer EML may include a material known in the art. For example, the light emitting layer EML may further include a fluorescent material including any one selected from the group consisting of spiro-DPVBi, 2,2',7,7'-tetrakis(biphenyl-4-yl)-9,9'-spirobifluorene (spiro-6P), distyryl-benzene (DSB), distyryl-arylene (DSA), a polyfluorene (PFO)-based polymer, and a poly(p-phenylene vinylene) (PPV)-based polymer. For example, the light emitting layer EML may include an anthracene compound, an arylamine compound, or a styryl compound. Furthermore, the light emitting layer EML may include a phosphorescent material known in the art.

The light emitting layer EML may include a host and a dopant. The host is not particularly limited to a particular material as long as the material is generally available in the art. For example, the host may include tris(8-hydroxyquinolino)aluminum (Alq3), 4,4'-bis(N-carbazolyl)-1,1'-biphenyl (CBP), poly(n-vinylcabazole) (PVK), 9,10-di(naphthalene-2-yl)anthracene (ADN), 4,4',4''-Tris(carbazol-9-yl)-triphenylamine (TCTA), 1,3,5-tris(N-phenylbenzimidazole-2-yl)benzene (TPBi), 3-tert-butyl-9,10-di(naphth-2-yl) anthracene (TBADN), distyrylarylene (DSA), 4,4-bis(9-carbazolyl)-2,2'-dimethyl-biphenyl (CDBP), 2-Methyl-9,10-bis(naphthalen-2-yl)anthracene (MADN), bis[2-(diphenylphosphino)phenyl]ether oxide (DPEPO), Hexaphenyl cyclotriphosphazene (CP1), 1,4-Bis(triphenylsilyl)benzene (UGH2), Hexaphenylcyclotrisiloxane (DP-SiO3), Octaphenylcyclotetra siloxane (DPSiO4), 2,8-Bis (diphenylphosphoryl)dibenzofuran (PPF), and the like may be used.

The dopant may be, for example, a styryl derivative (for example, 1,4-bis[2-(3-N-ethylcarbazoryl)vinyl]benzene (BCzVB), 4-(di-p-tolylamino)-4'-[(di-p-tolylamino)styryl] stilbene(DPAVB), and N-(4-((E)-2-(6-((E)-4-(d iphenylamino)styryl)naphthalen-2-yl)vinyl)phenyl)-N-phenylbenz enamine(N-BDAVBi), perylene and a derivative thereof (for example, 2,5,5,8,11-tetra-t-butylperylene (TBP)), pyrene and a derivative thereof (for example, 1,1-dipyrene, 1,4-dipyrenylbenzene, and 1,4-Bis(N, N-Diphenylamino)pyrene, Ir(ppy)$_3$([bis-(1-phenylisoquinolyl) iridium(III) acetylacetonate]), Ir(dpbic)$_3$, TPD, and the like.

The light emitting layer EML may emit phosphorescent light, or fluorescent light. Also, the light emitting layer EML may emit thermally activated delayed fluorescent light.

The light emitting layer EML may emit one of red light, green light, blue light, white light, yellow light, and cyan light.

The electron transport region ETR is provided on the light emitting layer EML. The electron transport region ETR may include at least one of the hole blocking layer, the electron transport layer ETL, or the electron injection layer EIL, but is not limited thereto.

The electron transport region ETR may have a single layer structure having a single layer formed of a single material, a single layer structure having a single layer formed of a plurality of different materials, or a multilayer structure having a plurality of layers formed of a plurality of different materials.

For example, the electron transport region ETR may have a single layer structure having a single layer of the electron injection layer EIL or the electron transport layer ETL, or a single layer structure having a single layer formed of an electron injection material and an electron transport material. Also, the electron transport region ETR may have a single layer structure having a single layer formed of a plurality of different materials, or have a structure of the electron transport layer ETL/the electron injection layer EIL, a hole blocking layer/the electron transport layer ETL/ the electron injection layer EIL, sequentially laminated on the first electrode EL1, but is not limited thereto. The thickness of the electron transport region ETR may be, for example, about 1000 Å to about 1500 Å.

The electron transport region ETR may be provided by various suitable methods such as vacuum deposition, spin coating, casting, Langmuir-Blodgett (LB), inkjet printing, laser printing, and laser induced thermal imaging (LITI).

When the electron transport region ETR includes the electron transport layer ETL, the electron transport region ETR may include an anthracene-based compound, but is not limited thereto. The electron transport region ETR may include Tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-Tri (1-phenyl-1H-benzo[d]imidazol-2-yl)phenyl (TPBi), 2,9-Dimethyl-4,7-diphenyl-1,10-phenanthroline (BCP), 4,7-Diphenyl-1,10-phenanthroline (Bphen), 3-(4-Biphenylyl)-4-phenyl-5-tert-butylphenyl-1,2,4-triazole (TAZ), 4-(Naphthalen-1-yl)-3,5-diphenyl-4H-1,2,4-triazole (NTAZ), 2-(4-BiphenylyI)-5-(4-tert-butylphenyl)-1,3,4-oxadiazole (tBu-PBD), Bis(2-methyl-8-quinolinolato-N1, O8)-(1,1'-Biphenyl-4-olato)aluminum (BAlq), Berylliumbis (benzoquinolin-10-olate (Bebq$_2$), 9,10-di(naphthalene-2-yl) anthracene (ADN), and a mixture thereof. The thicknesses of the electron transport layers ETL may be about 100 Å to about 1000 Å, for example, about 150 Å to about 500 Å. When the thicknesses of the electron transport layers ETL satisfy the above-described ranges, a suitable or satisfactory electron transport characteristic may be obtained without a substantial increase in driving voltage.

When the electron transport region ETR includes the electron injection layer EIL, the electron transport region ETR may be formed of a lanthanide group metal such as LiF, Lithium quinolate (LiQ), Li$_2$O, BaO, NaCl, CsF and Yb, or of a halogenated metal such as RbCl and RbI, but is not limited thereto. The electron injection layer EIL may be formed of a mixture of an electron transport material and an insulating organo metal salt. The organo metal salt may be a material having an energy band gap of about 4 eV or greater. For example, the organo metal salt may include metal acetate, metal benzoate, metal acetoacetate, metal acetylacetonate, or metal stearate. The thicknesses of the electron injection layers EIL may be about 1 Å to about 100 Å, and about 3 Å to about 90 Å. When the thicknesses of the electron injection layers EIL satisfy the above-described ranges, a suitable or satisfactory electron injection characteristic may be obtained without a substantial increase in driving voltage.

The electron transport region ETR may include the hole blocking layer as mentioned above. The hole blocking layer may include at least one of, for example, 2,9-dimethyl-4,7-diphenyl-1,10-phenanthroline (BCP) and 4,7-diphenyl-1, 10-phenanthroline (Bphen), but is not limited thereto.

The second electrode EL2 is provided on the electron transport region ETR. The second electrode EL2 may be a common electrode or a negative electrode. The second electrode EL2 may be a transmissive electrode, a transflective electrode, or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), and the like.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, or a compound or a mixture thereof (for example, a mixture of Ag and Mg). Also, the second electrode EL2 may have a multilayer structure including a reflective film or a transflective film, both formed of the above materials, and a transparent conductive film formed of indium tin oxide (ITO), indium zinc oxide (IZO), zinc oxide (ZnO), indium tin zinc oxide (ITZO), and the like.

The second electrode EL2 may be connected to an auxiliary electrode. When the second electrode EL2 is connected to the auxiliary electrode, the resistance of the second electrode EL2 may be reduced.

In the organic electroluminescence device 10, as voltage is applied to each of the first electrode EL1 and the second electrode EL2, a hole injected from the first electrode EL1 is moved to the light emitting layer EML through the hole transport region HTR, and an electron injected from the second electrode EL2 is moved to the light emitting layer EML through the electron transport region ETR. The electron and the hole are recombined in the light emitting layer EML to generate an exciton, and the exciton falls to a ground state from an excited state to emit light.

When the organic electroluminescence device 10 is a top emission type, the first electrode EL1 may be a reflective electrode, and the second electrode EL2 may be a transmissive electrode or a transflective electrode. When the organic electroluminescence device 10 is a bottom emission type, the first electrode EL1 may be a transmissive electrode or a transflective electrode, and the second electrode EL2 may be a reflective electrode.

The organic electroluminescence device 10 according to an embodiment of the present disclosure provides the light absorbing layer LA including a light absorber represented by Formula 1 on at least one of a lower portion of the first electrode EL1 and an upper portion of the second electrode EL2 to efficiently prevent ultraviolet light and a part of visible light from entering into the light emitting layer EML (or to efficiently prevent ultraviolet light and a part of visible light from entering into the light emitting layer EML), so that stability, efficiency, and lifespan characteristics are improved.

Hereinafter, an organic electroluminescence device according to an embodiment of the present disclosure will be described. Hereinafter, differences from the light absorber according to an embodiment of the present disclosure will be described in more detail. Parts that are not described below correspond to the light absorber according to an embodiment of the present disclosure.

Referring to FIGS. 1-5, an organic electroluminescence device 10 according to an embodiment of the present disclosure includes the first electrode EL1, the hole transport region HTR, the light emitting layer EML, the electron transport region ETR, the second electrode EL2, and the light absorbing layer LA. The light absorbing layer LA includes a light absorber including a polycyclic aromatic compound, and the polycyclic aromatic compound is substituted with a substituent including a structure represented by Formula A below.

Formula A

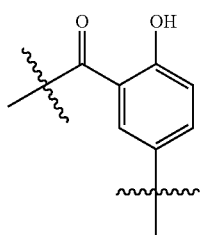

In Formula A above,

are each independently a position substituted with the polycyclic aromatic compound or a position substituted with a hydrogen atom or a substituted or unsubstituted aryl group having 6 to 30 ring-forming carbon atoms.

"A substituent including a structure represented by Formula A" means that a structure represented by Formula A is included in the substituent structure, and for example, a structure in which another substituent is further substituted in the structure represented by Formula A may be included. "A substituent including a structure represented by Formula A" may be represented, for example, by any one of Formula 2-1 to 2-3 described above.

The polycyclic aromatic compound may be, for example, a bicyclic, tricyclic or tetracyclic aromatic compound. The polycyclic aromatic compound may include, for example, pyrene, chrysene, or anthracene.

The polycyclic aromatic compound may have a structure further substituted with a substituent other than a substituent including a structure represented by Formula A. For example, the polycyclic aromatic compound may further be substituted with a substituted or unsubstituted alkyl group having 1 to 20 carbon atoms, a substituted or unsubstituted alkenyl group having 2 to 20 carbon atoms, a substituted or unsubstituted alkoxy group having 1 to 20 carbon atoms, a substituted or unsubstituted acrylate group having 1 to 20 carbon atoms, a substituted or unsubstituted aryl group having 6 to 30 ring-forming carbon atoms, a substituted or unsubstituted heteroaryl group having 2 to 30 ring-forming carbon atoms, a substituted or unsubstituted carbonyl group, a substituted or unsubstituted benzophenone group, a substituted or unsubstituted benzoate group, or a substituted or unsubstituted salicylate.

The polycyclic aromatic compound may further be substituted with a substituted or unsubstituted aryl group having 6 to 15 ring-forming carbon atoms, or with a substituted or unsubstituted polycyclic heteroaryl group. The polycyclic aromatic compound may further be substituted with a substituted or unsubstituted phenyl group, a substituted or unsubstituted biphenyl group, a substituted or unsubstituted naphthyl group, a substituted or unsubstituted anthracene group, a substituted or unsubstituted phenanthrene group, a substituted or unsubstituted dibenzofuran group, or a substituted or unsubstituted dibenzothiophene group.

The polycyclic aromatic compound may further be substituted a substituted or unsubstituted phenyl group, or with a substituted or unsubstituted biphenyl group, and when a phenyl group and a biphenyl group are substituted, a substituent may further be substituted with, for example, an alkoxy group having 1 to 10 carbon atoms.

The polycyclic aromatic compound may further be substituted with a substituent represented by Formula 3 described above.

The polycyclic aromatic compound may be substituted by any one of the following structural formulas.

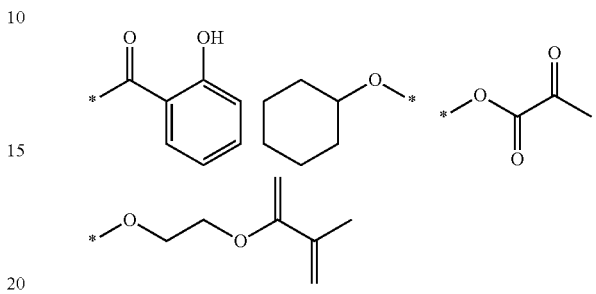

In the structural formulas above, -* means a portion to be connected to the polycyclic aromatic compound.

The polycyclic aromatic compound may be at least one selected from the compounds represented by Compound group 1 described above.

Hereinafter, embodiments of the present disclosure will be described in more detail with reference to the following examples and comparative examples. The following examples are merely exemplary for the understanding the subject matter of the present disclosure, and the scope of the present disclosure is not limited thereto.

Synthesis Example 1

A light absorber according to an embodiment of the present disclosure may be synthesized, for example, as follows. However, a method for synthesizing a light absorber according to an embodiment of the present disclosure is not limited thereto.

1. Synthesis of Compound 1

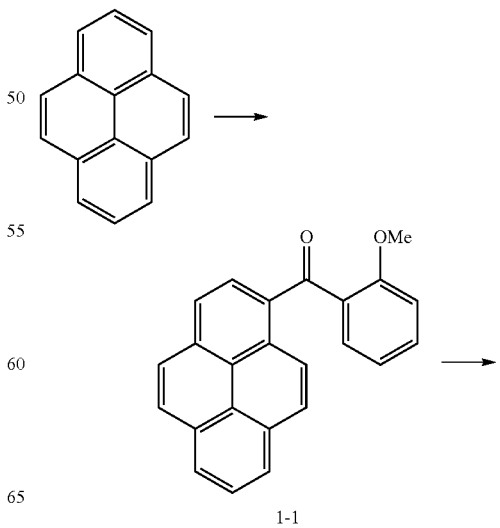

1-1

Synthesis of Intermediate 1-1

2.02 g (10 mmol) of pyrene and 1.701 g of 2-methoxybenzoyl chloride were dissolved in 50 mL of MC, and then 1.333 g of AlCl3 was slowly added thereto. The temperature of the reaction solution was raised to room temperature and stirred at room temperature for 6 hours. After the reaction was completed, 30 mL of H₂O was added thereto and the mixture was extracted three times with 30 mL of MC to obtain an organic layer. The obtained organic layer was dried with magnesium sulfate and the solvent was evaporated to obtain a residue. The obtained residue was separated and purified by silica gel column chromatography to obtain 3.363 g of Intermediate 1-1 (Yield 100%).

(Synthesis of Compound 1)

3.363 g (10 mmol) of Intermediate 1-1 was dissolved in 50 mL of MC, and then 5.58 mL (60 mmol) of BBr3 was slowly added dropwise at 0° C. The temperature of the reaction solution was raised to room temperature and stirred at room temperature for 24 hours. After the reaction was completed, 30 mL of H2O was added thereto and the mixture was extracted three times with 30 mL of MC to obtain an organic layer. The obtained organic layer was dried with magnesium sulfate and the solvent was evaporated to obtain a residue. The obtained residue was separated and purified by silica gel column chromatography to obtain 2.254 g of Compound 1 (Yield 70%).

2. Synthesis of Compound 9

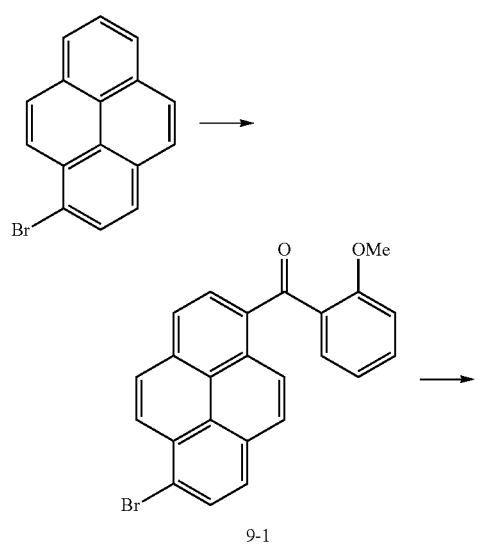

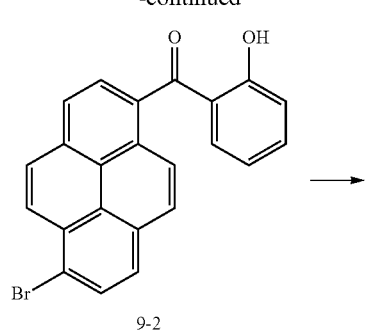

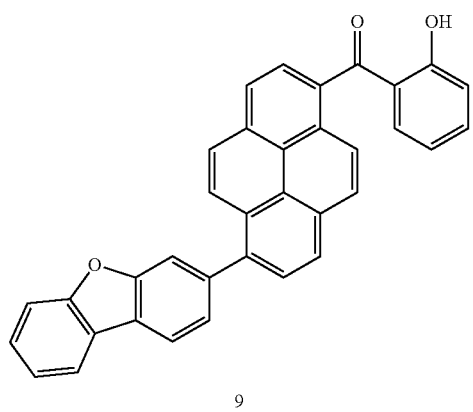

Synthesis of Intermediate 9-1

4.152 g (Yield 100%) of Intermediate 9-1 was obtained in substantially the same manner as in the synthesis of Intermediate 1-1, except that 1-bromopyrene was used instead of pyrene.

Synthesis of Intermediate 9-2

4.895 g (Yield 100%) of Intermediate 9-2 was obtained in substantially the same manner as in the synthesis of Compound 1, except that Intermediate 9-1 was used instead of Intermediate 1-1.

Synthesis of Compound 9

Under a nitrogen atmosphere, 4.895 g (10 mmol) of Intermediate 9-2, 2.121 g (10 mmol) of 3-dibenzofuranboronic acid, 0.578 g (0.5 mmol) of Pd (PPh₃)₄, and 2.762 g (20 mmol) of K₂CO₃ were dissolved in 100 mL of THF/H₂O (2/1 by volume ratio) solution, and the mixture was stirred at 80° C. for 12 hours.

After the reaction solution was cooled to room temperature, 30 mL of H₂O was added thereto and the mixture was extracted three times with 50 mL of ethyl ether to obtain an organic layer. The obtained organic layer was dried with magnesium sulfate and the solvent was evaporated to obtain a residue. The obtained residue was separated and purified by silica gel column chromatography to obtain 3.416 g (7 mmol, Yield 70%) of Compound 9.

3. Synthesis of Compound 15

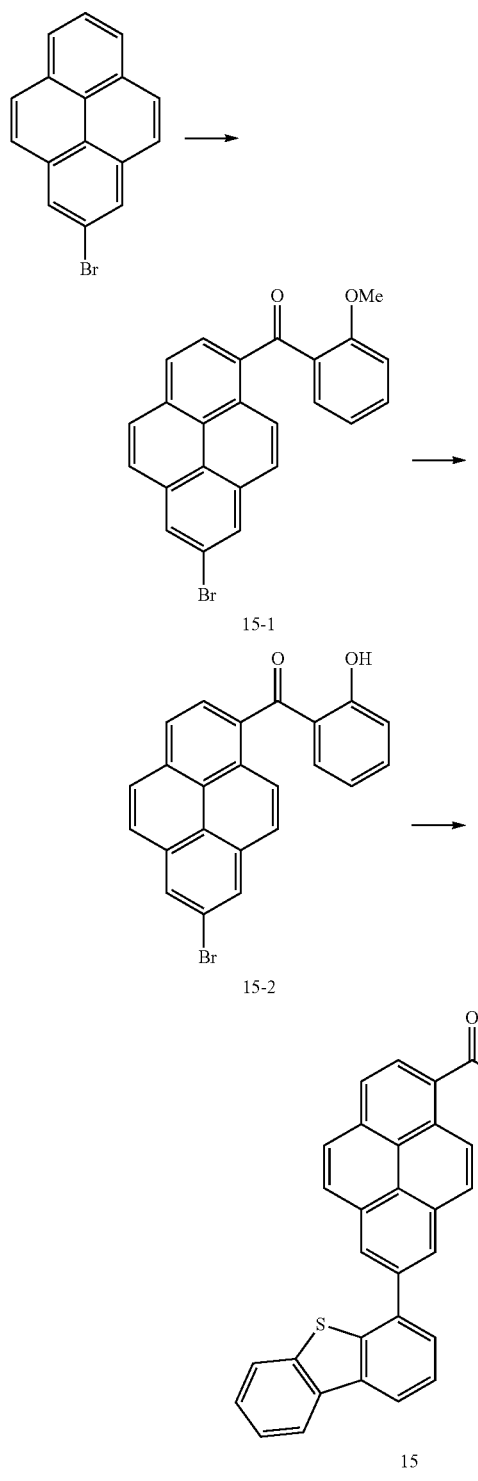

Synthesis of Intermediate 15-1

4.152 g (Yield 100%) of Intermediate 15-1 was obtained in substantially the same manner as in the synthesis of Intermediate 1-1, except that 2-bromopyrene was used instead of pyrene.

(Synthesis of Intermediate 15-2)

4.895 g (Yield 100%) of Intermediate 15-2 was obtained in substantially the same manner as in the synthesis of Compound 1, except that Intermediate 15-1 was used instead of Intermediate 1-1.

Synthesis of Compound 15

3.415 g (Yield 70%) of Compound 15 was obtained in substantially the same manner as in the synthesis of Compound 9, except that Intermediate 15-2 was used instead of Intermediate 9-2, and 4-dibenzothiophene boronic acid was used instead of 3-dibenzofuran boronic acid.

4. Synthesis of Compound 27

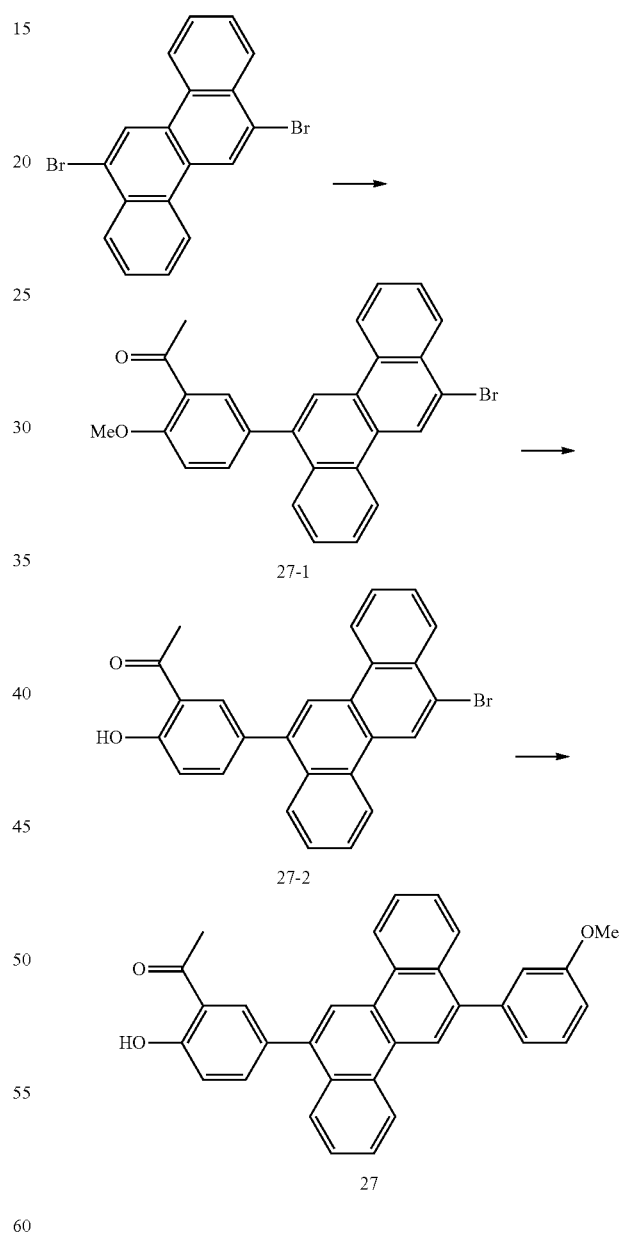

Synthesis of Intermediate 27-1

3.185 g (Yield 70%) of Intermediate 27-1 was obtained in substantially the same manner as in the synthesis of Compound 9, except that 6,12-dibromoklicene was used instead of Intermediate 9-2, and (3-acetyl-4-methoxyphenyl) boronic acid was used instead of 3-dibenzofuran boronic acid.

(Synthesis of Intermediate 27-2)

3.087 g (Yield 100%) of Intermediate 27-2 was obtained in substantially the same manner as in the synthesis of Compound 1, except that Intermediate 27-1 was used instead of Intermediate 1-1.

Synthesis of Compound 27

2.293 g (Yield 70%) of Compound 27 was obtained in substantially the same manner as in the synthesis of Compound 9, except that Intermediate 27-2 was used instead of Intermediate 9-2, and 3-anisol boronic acid was used instead of 3-dibenzofuran boronic acid.

5. Synthesis of Compound 35

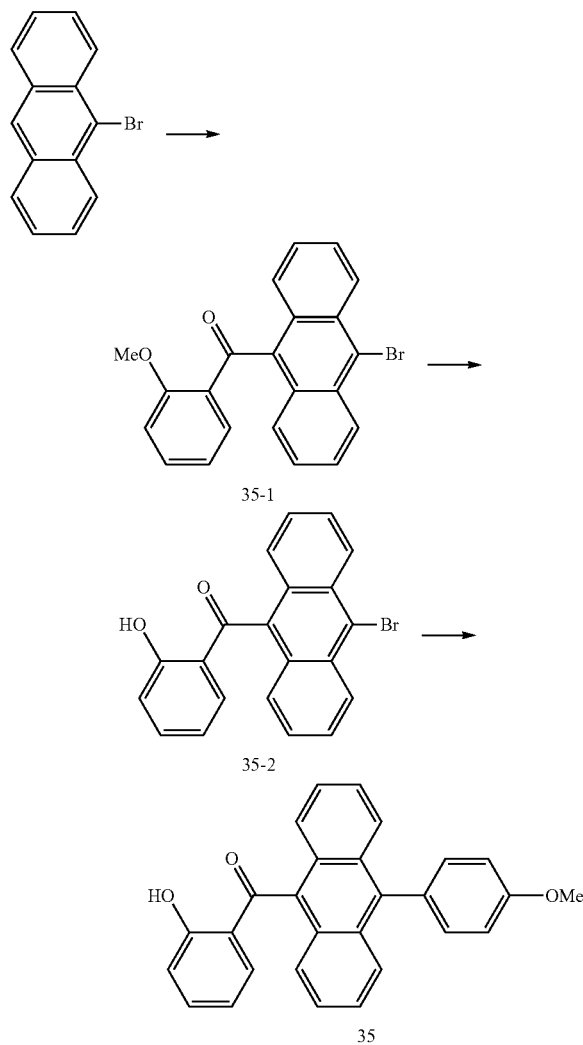

Synthesis of Intermediate 35-1

3.912 g (Yield 100%) of Intermediate 35-1 was obtained in substantially the same manner as in the synthesis of Intermediate 1-1, except that 9-bromoanthracene was used instead of pyrene.

Synthesis of Intermediate 35-2

3.772 g (Yield 100%) of Intermediate 35-2 was obtained in substantially the same manner as in the synthesis of Compound 1, except that Intermediate 35-1 was used instead of Intermediate 1-1.

Synthesis of Compound 35

2.828 g (Yield 70%) of Compound 35 was obtained in substantially the same manner as in the synthesis of Compound 9, except that Intermediate 35-2 was used instead of Intermediate 9-2, and 4-anisol boronic acid was used instead of 3-dibenzofuran boronic acid.

6. Synthesis of Compound 41

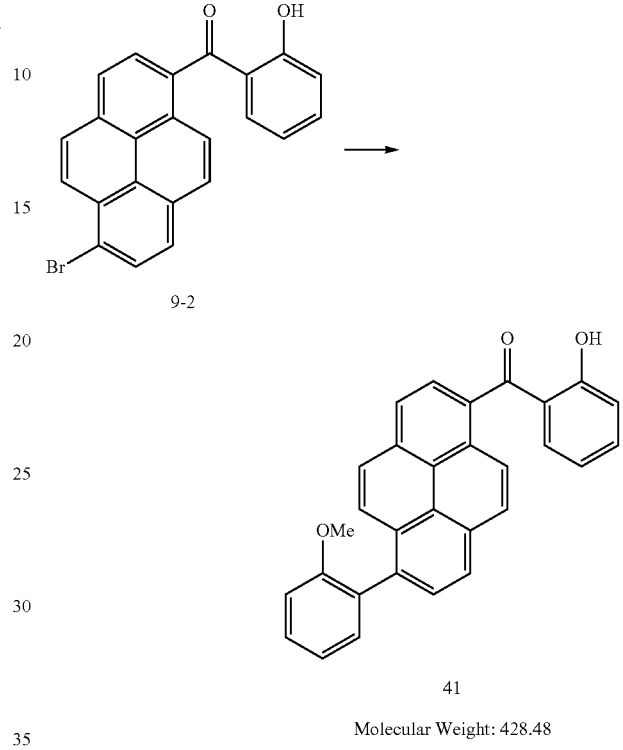

Molecular Weight: 428.48

4.152 g (Yield 80%) of Compound 41 was obtained in substantially the same manner as in the synthesis of Compound 9, except that 2-methoxy-bromopyrene was used instead of 3-dibenzofuran boronic acid.

NMR and molecular weight analysis data of Compounds 1, 9, 15, 27, 35, and 41 synthesized in Synthesis Examples are shown in Table 1 below.

TABLE 1

| Compound | $^1$H NMR (CDCl$_3$, 300 MHz) | LC/MS found | calc. |
|---|---|---|---|
| 1 | 9.0 (d, 1H) 8.5-8.0 (m, 8H), 7.8 (m, 2H), 7.2 (d, 1H), 7.1 (dd, 1H) | 323.20 | 322.10 |
| 9 | 9.1 (d, 1H) 8.4-8.0 (m, 8H), 7.8-7.4 (m, 8H), 7.2 (d, 1H), 7.0 (dd, 1H) | 489.25 | 488.14 |
| 15 | 9.0 (d, 1H) 8.6-8.1 (m, 11H), 7.9-7.4 (m, 5H), 7.3 (d, 1H), 7.2 (m, 1H) | 505.65 | 504.60 |
| 27 | 8.6 (d, 4H) 8.0-7.4 (m, 10H), 7.1-6.9 (m, 3H), 3.8 (s, 3H), 2.2 (s, 3H) | 469.28 | 468.17 |
| 35 | 8.6 (d, 2H) 7.8-7.4 (m, 7H), 7.3 (d, 4H), 7.0-6.9 (d, 4H), 4.0 (s, 3H) | 405.10 | 404.14 |
| 41 | 8.4 (d, 2H) 7.8-7.5 (m, 8H), 7.4 -7.1 (m, 5H), 7.0-6.8 (d, 3H), 3.8 (s, 3H) | 429.25 | 428.14 |

The light transmittance of Compounds 1, 9, 15, 27, 35, and 41 synthesized in the Synthesis Examples are shown in Table 2 below.

TABLE 2

| Example | Example Compound | Transmittance (@ 405 nm) | Transmittance (@ 430 nm) |
|---|---|---|---|
| Example 1 | Compound 1 | 3.38 | 40.18 |
| Example 2 | Compound 9 | 7.54 | 75.15 |
| Example 3 | Compound 15 | 1.68 | 29.47 |
| Example 4 | Compound 27 | 4.12 | 48.21 |
| Example 5 | Compound 35 | 4.54 | 50.52 |
| Example 6 | Compound 41 | 3.20 | 45.15 |

The results in Table 2 are values measured in a toluene solvent at $10^{-5}$ M concentration using Shimazu UV-1800.

Referring to Table 2, the compounds of Examples 1 to 6 have excellent light absorbance in set or specific wavelength regions. For example, the compounds of Examples 1 to 6 have a high light absorbance at 380 nm to 410 nm, and more specifically, have a degree of light absorbance of 0.7 or more in a wavelength range of 380 nm to 410 nm.

A light absorber according to an embodiment of the present disclosure has excellent light absorbance for ultraviolet light and a part of visible light, and an organic electroluminescence device using the same in a light absorbing layer is efficiently prevented from deterioration due to external light (or such deterioration is efficiently reduced), thereby having excellent efficiency and lifespan characteristics.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The embodiments described herein are to be considered illustrative and not restrictive, and the appended claims are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A light absorber represented by Formula 1 below:

Formula 1 wherein in Formula 1,

Ar is pyrene, chrysene, or anthracene,

Y is a substituted or unsubstituted alkyl group having 1 to 20 carbon atoms, a substituted or unsubstituted alkenyl group having 2 to 20 carbon atoms, a substituted or unsubstituted alkoxy group having 1 to 20 carbon atoms, a substituted or unsubstituted acrylate group having 1 to 20 carbon atoms, a substituted or unsubstituted aryl group having 6 to 30 ring-forming carbon atoms, a substituted or unsubstituted heteroaryl group having 2 to 30 ring-forming carbon atoms, a substituted or unsubstituted carbonyl group, a substituted or unsubstituted benzophenone group, a substituted or unsubstituted benzoate group, or a substituted or unsubstituted salicylate, and X is represented by any one of Formula 2-1 to 2-3 below:

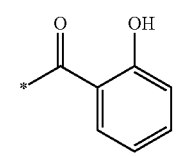

Formula 2-1

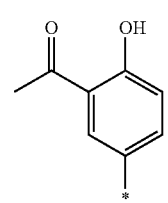

Formula 2-2

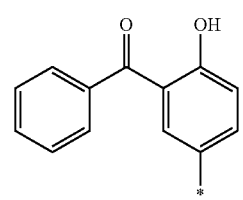

Formula 2-3

2. The light absorber of claim 1, wherein Formula 1 above is represented by any one of Formula 1-1 to 1-3 below:

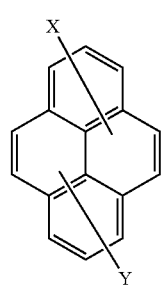

Formula 1-1

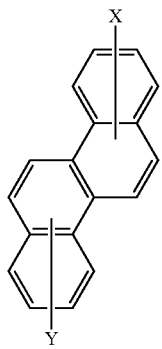

Formula 1-2

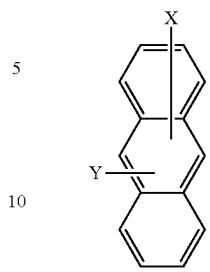

Formula 1-6 wherein in Formula 1-4 to 1-6 above, X and Y are the same as defined in Formula 1.

4. The light absorber of claim 1, wherein Formula 1 above is represented by any one of Formula 1-7 to 1-9 below:

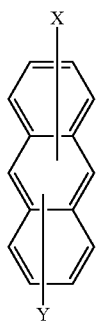

Formula 1-3

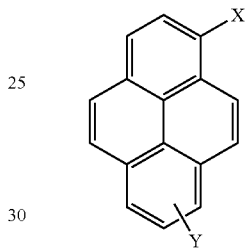

Formula 1-7 wherein in Formula 1-1 to 1-3 above, X and Y are the same as defined in Formula 1.

3. The light absorber of claim 1, wherein Formula 1 above is represented by any one of Formula 1-4 to 1-6 below:

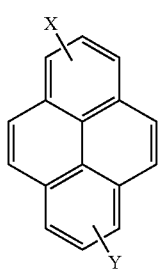

Formula 1-4

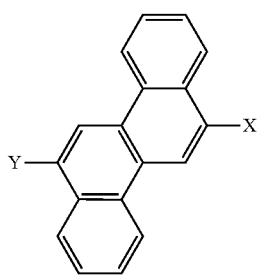

Formula 1-8

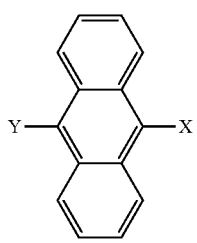

Formula 1-9

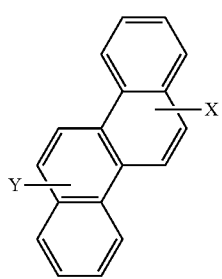

Formula 1-5 wherein in Formula 1-7 to 1-9 above, X and Y are the same as defined in Formula 1.

5. The light absorber of claim 1, wherein Y is a substituted or unsubstituted phenyl group, a substituted or unsubstituted biphenyl group, a substituted or unsubstituted naphthyl group, a substituted or unsubstituted anthracene group, a substituted or unsubstituted phenanthrene group, a substituted or unsubstituted dibenzofuran group, or a substituted or unsubstituted dibenzothiophene group.

6. The light absorber of claim 1, wherein Y is represented by any one of the following structural formulas:

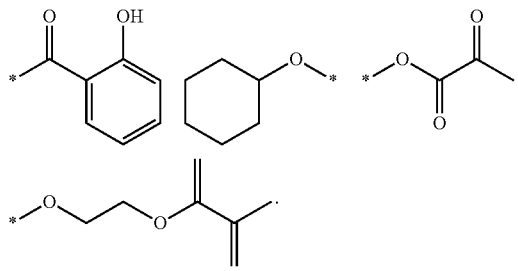

7. The light absorber of claim 1, wherein X is represented by Formula 2-1, and Y is represented by Formula 3 below:

Formula 3

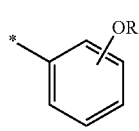

wherein in Formula 3, R is a substituted or unsubstituted alkyl group having 1 to 5 carbon atoms.

8. The light absorber of claim 1 having an absorbance of 0.7 or more in a wavelength range of 380 nm to 410 nm.

9. The light absorber of claim 1, wherein the light absorber represented by Formula 1 above is any one selected from the compounds represented by Compound group 1 below:

Compound group 1

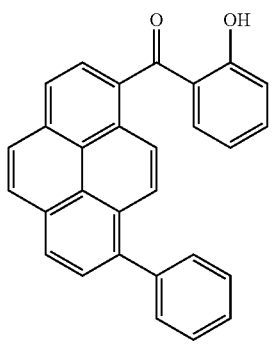

2

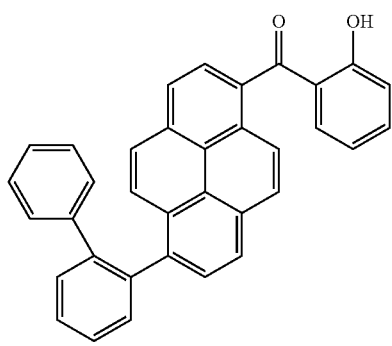

3

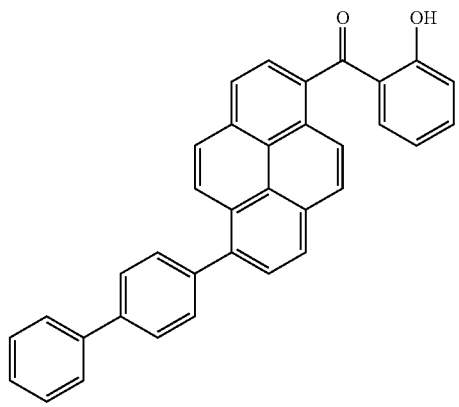

4

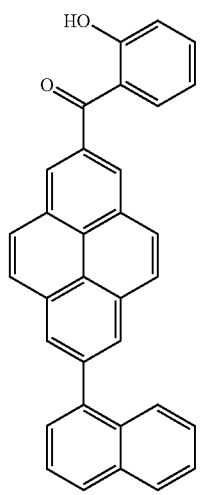

5

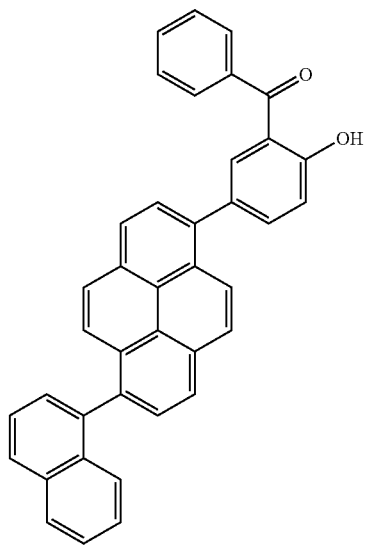

6

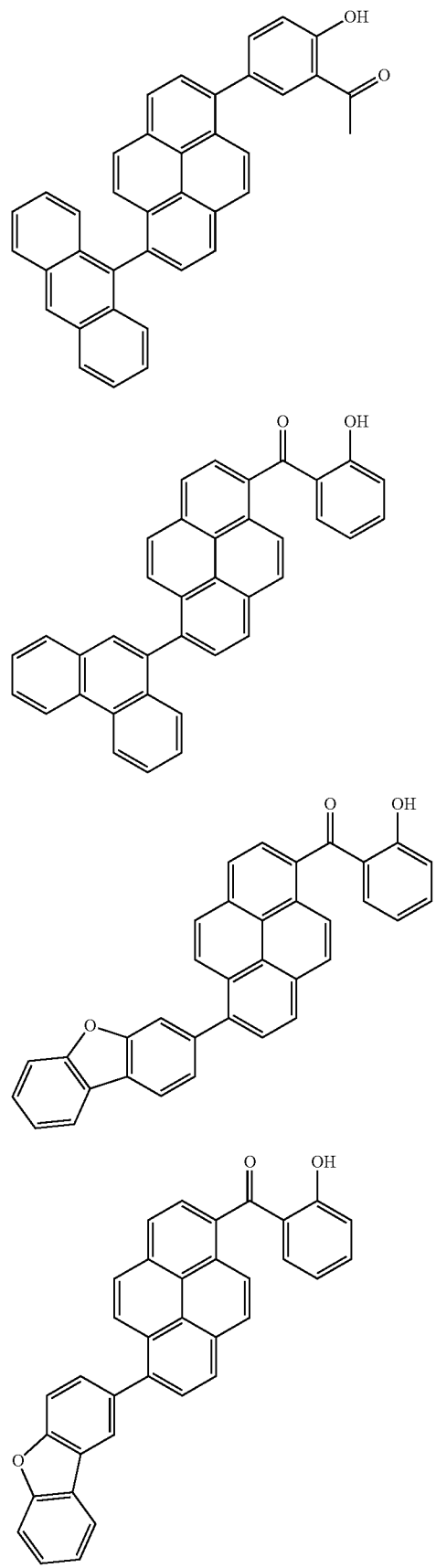
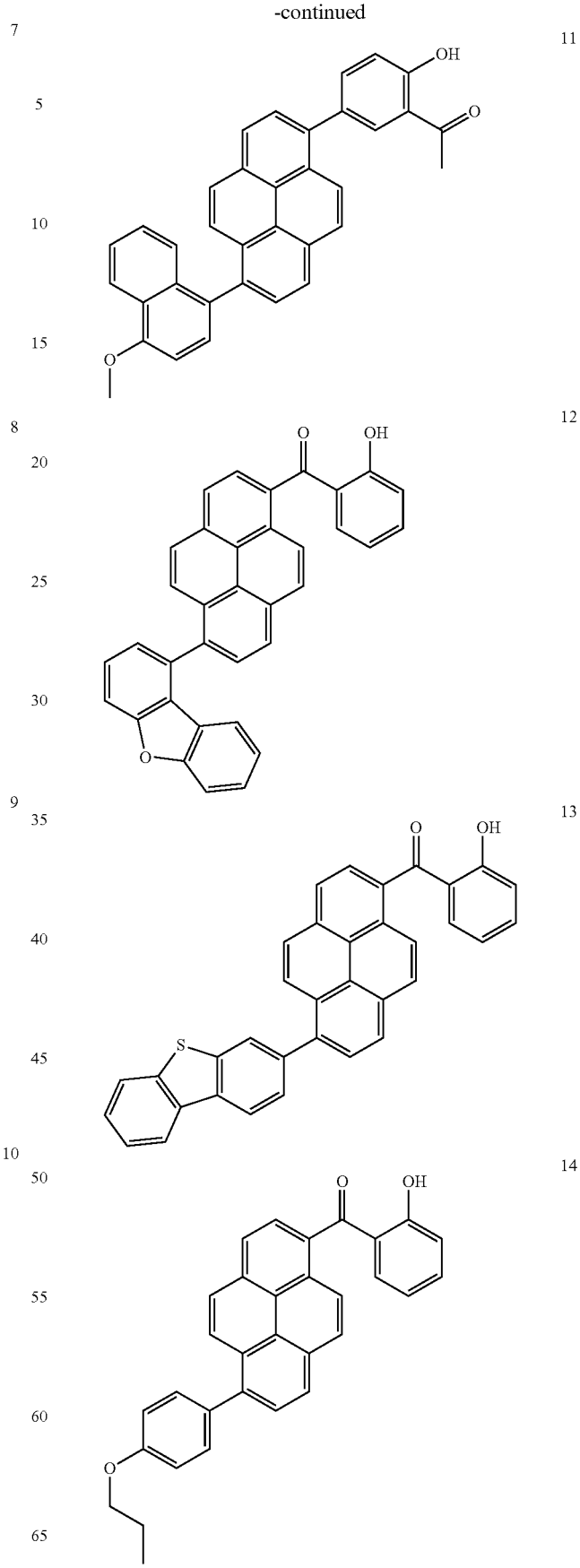

15
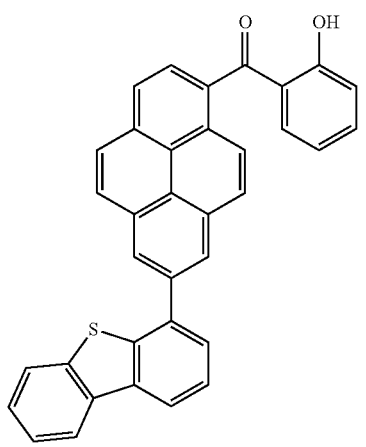
16
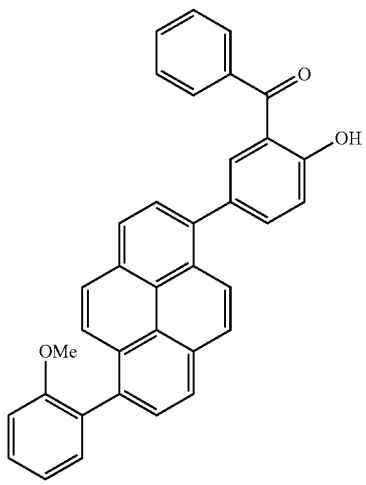
17
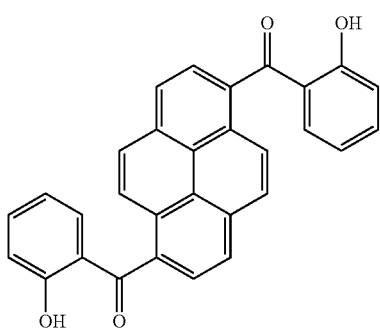
18
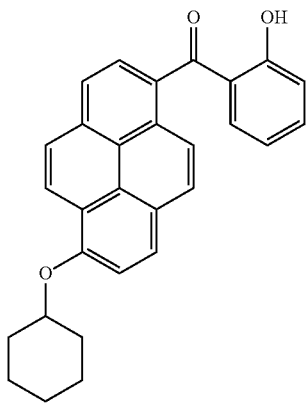
19
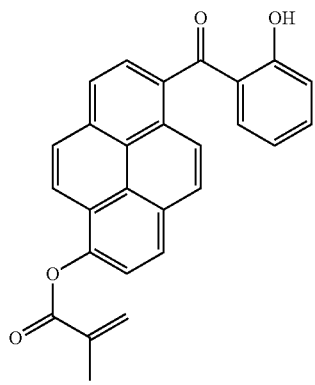
20
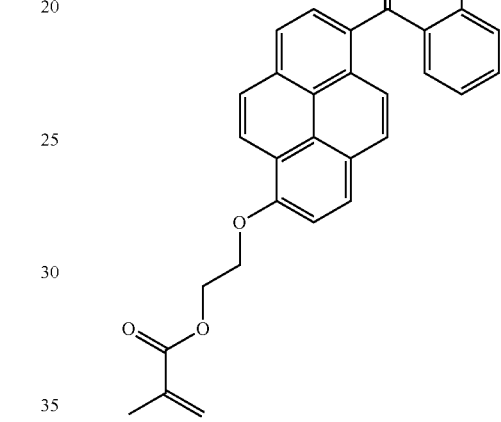
21
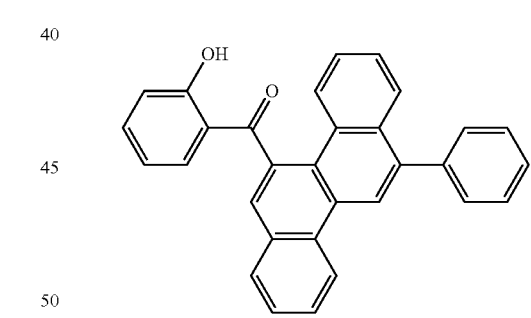
22
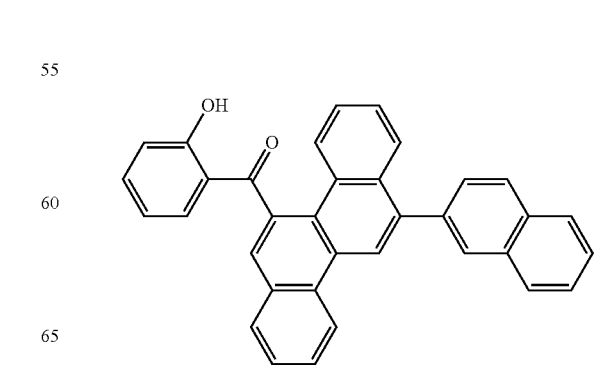

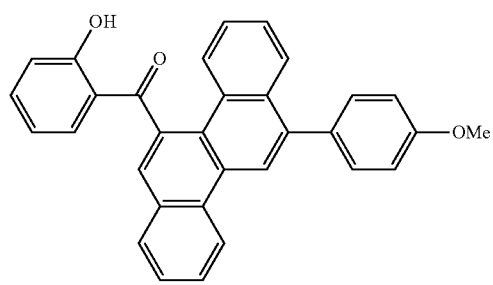
23
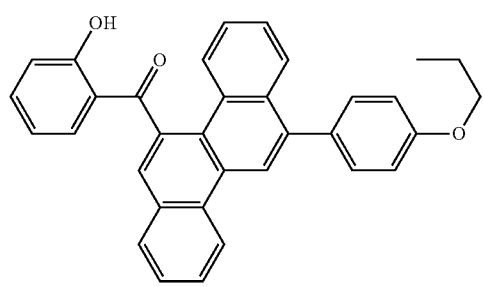
24
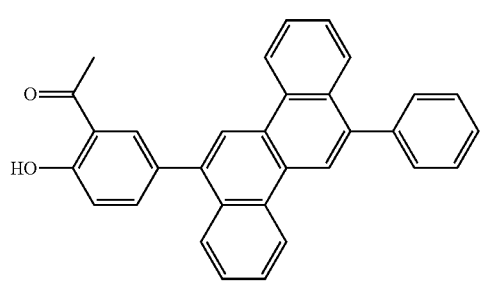
25
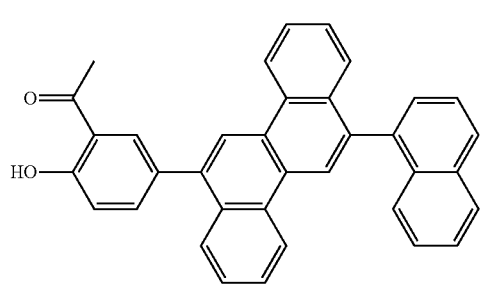
26
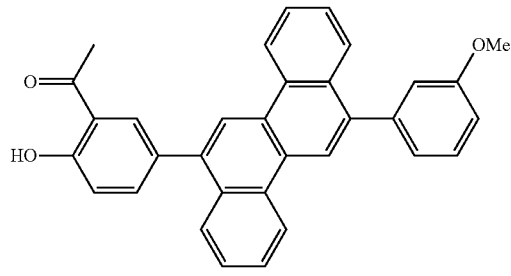
27
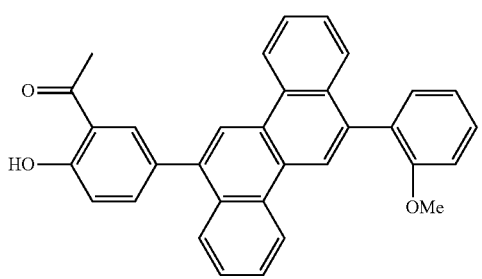
28
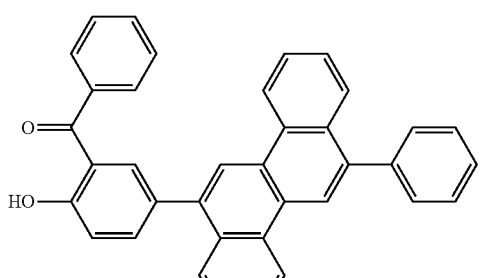
29
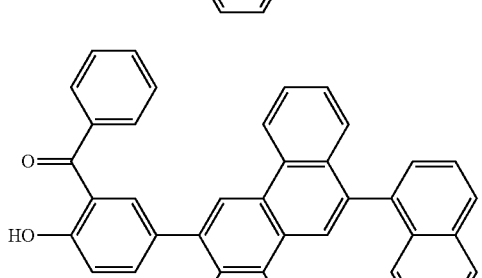
30
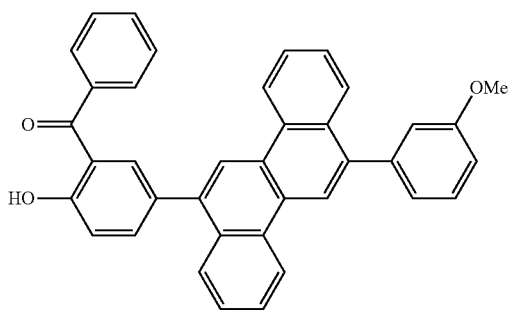
31
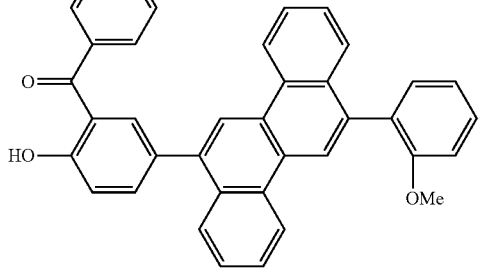
32

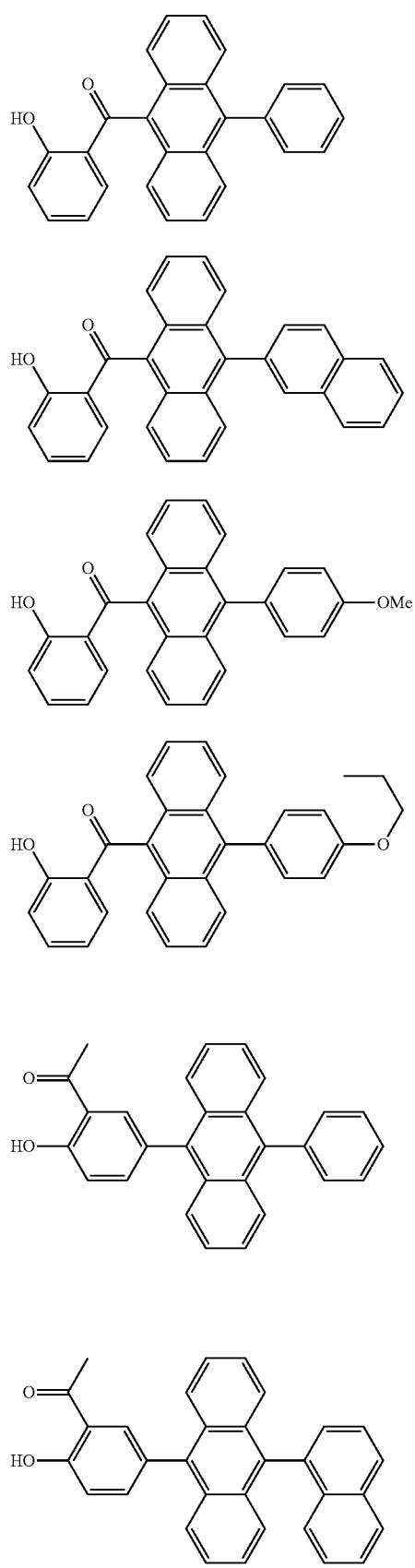
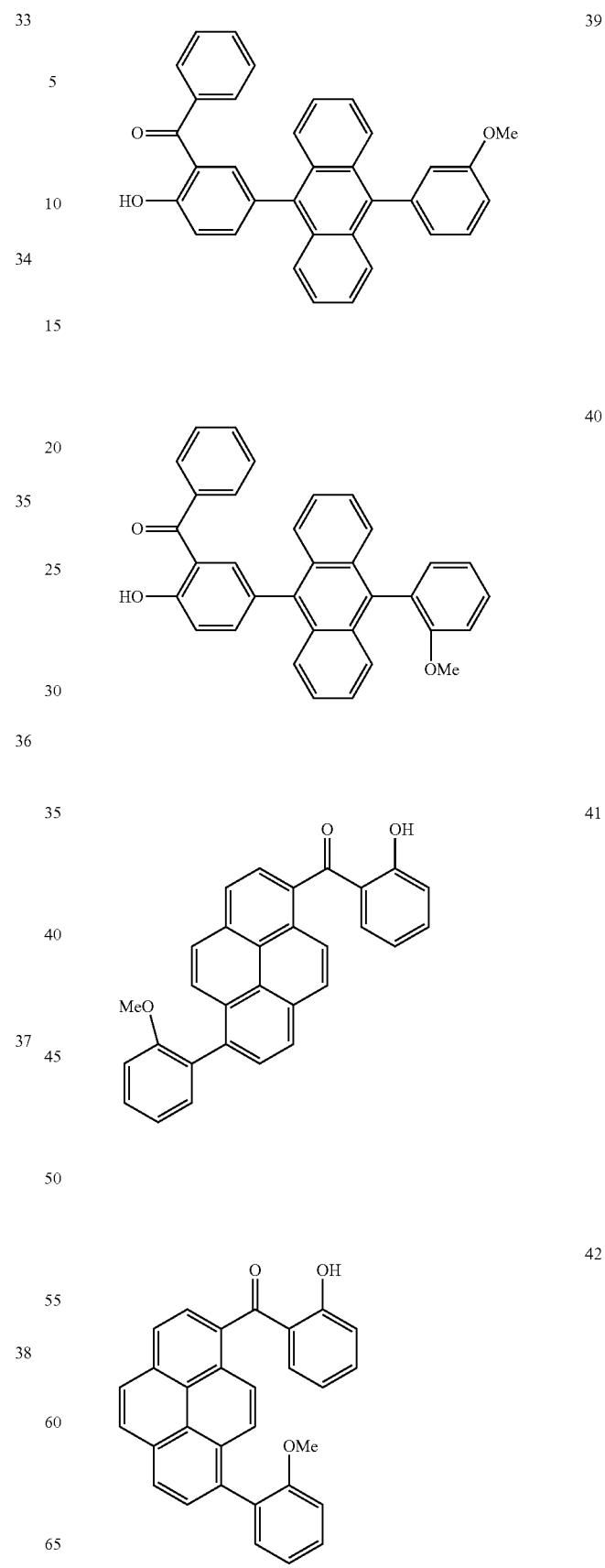

-continued

43

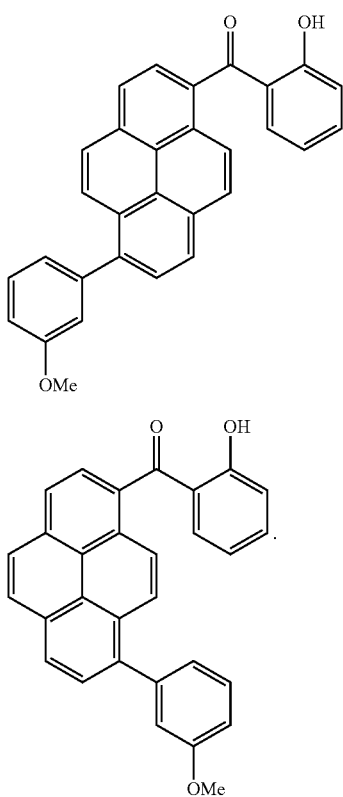

44

10. An organic electroluminescence device comprising:
a first electrode;
a hole transport region provided on the first electrode;
a light emitting layer provided on the hole transport region;
an electron transport region provided on the light emitting layer;
a second electrode provided on the electron transport region; and
a light absorbing layer provided on at least one of a lower portion of the first electrode or an upper portion of the second electrode,
wherein the light absorbing layer comprises a light absorber represented by formula 1 below:

X—Ar—Y      Formula 1 wherein in Formula 1 above,
Ar is pyrene, chrysene, or anthracene,
Y is a hydrogen atom, a substituted or unsubstituted alkyl group having 1 to 20 carbon atoms, a substituted or unsubstituted alkenyl group having 2 to 20 carbon atoms, a substituted or unsubstituted alkoxy group having 1 to 20 carbon atoms, a substituted or unsubstituted acrylate group having 1 to 20 carbon atoms, a substituted or unsubstituted aryl group having 6 to 30 ring-forming carbon atoms, a substituted or unsubstituted heteroaryl group having 2 to 30 ring-forming carbon atoms, a substituted or unsubstituted carbonyl group, a substituted or unsubstituted benzophenone group, a substituted or unsubstituted benzoate group, or a substituted or unsubstituted salicylate, and X is represented by any one of Formula 2-1 to 2-3 below.

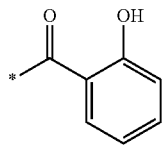
Formula 2-1

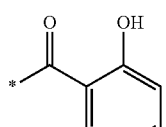
Formula 2-2

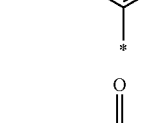
Formula 2-3

11. The organic electroluminescence device of claim 10, wherein Formula 1 above is represented by any one of Formula 1-1 to 1-3 below:

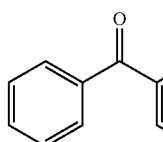
Formula 1-1

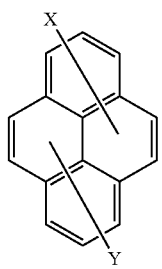
Formula 1-2

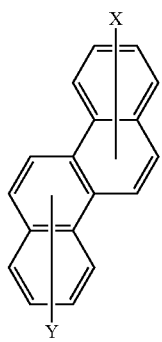
Formula 1-3 wherein in Formula 1-1 to 1-3 above, X and Y are the same as defined in Formula 1.

12. The organic electroluminescence device of claim 10, wherein Formula 1 above is represented by any one of Formula 1-4 to 1-6 below:

Formula 1-4

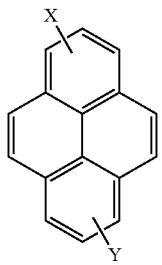

Formula 1-5

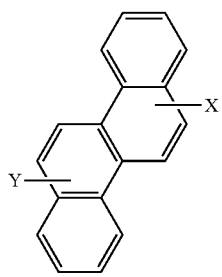

Formula 1-6

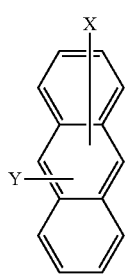

wherein in Formula 1-4 to 1-6 above, X and Y are the same as defined in Formula 1.

13. The organic electroluminescence device of claim 10, wherein Formula 1 above is represented by any one of Formula 1-7 to 1-9 below:

Formula 1-7

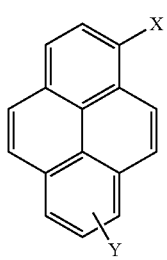

Formula 1-8

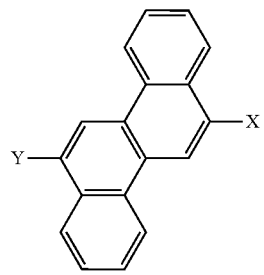

Formula 1-9

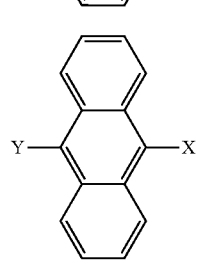

where in Formula 1-7 to 1-9 above, X and Y are the same as defined in Formula 1.

14. The organic electroluminescence device of claim 10, wherein Y is a substituted or unsubstituted phenyl group, a substituted or unsubstituted biphenyl group, a substituted or unsubstituted naphthyl group, a substituted or unsubstituted anthracene group, a substituted or unsubstituted phenanthrene group, a substituted or unsubstituted dibenzofuran group, or a substituted or unsubstituted dibenzothiophene group.

15. The organic electroluminescence device of claim 10, wherein Y is represented by any one of the following structural formulas:

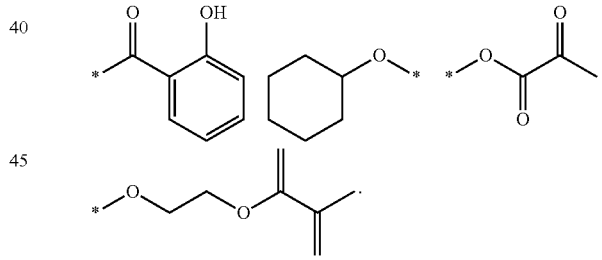

16. The organic electroluminescence device of claim 10, wherein X is represented by Formula 2-1, and Y is represented by Formula 3 below:

Formula 3

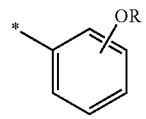

wherein in Formula 3 above, R is a substituted or unsubstituted alkyl group having 1 to 5 carbon atoms.

17. The organic electroluminescence device of claim 10, wherein the light absorber has an absorbance of 0.7 or more in a wavelength range of 380 nm to 410 nm.

18. The organic electroluminescence device of claim 10, wherein the light absorbing layer is disposed on the second electrode, and is in contact with the second electrode.

19. The organic electroluminescence device of claim 10, wherein the light absorbing layer is a thin film encapsulating layer covering the first electrode, the hole transport region, the light emitting layer, the electron transport region, and the second electrode.

20. The organic electroluminescence device of claim 10, wherein the light absorbing layer represented by Formula 1 above is at least one selected from the compounds represented by Compound group 1 below:

Compound group 1

1
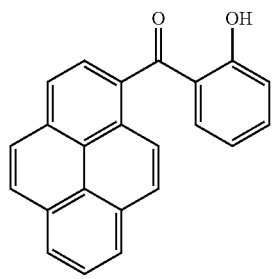

2
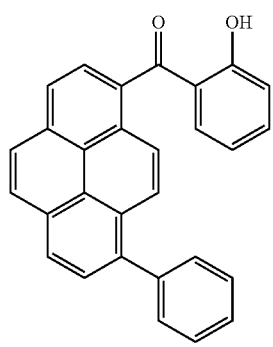

3
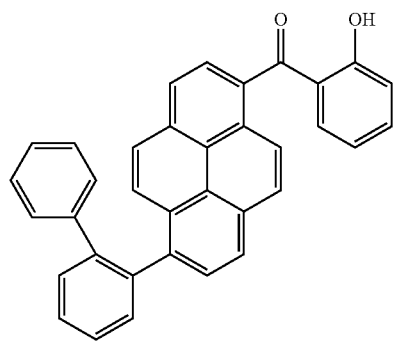

-continued

4
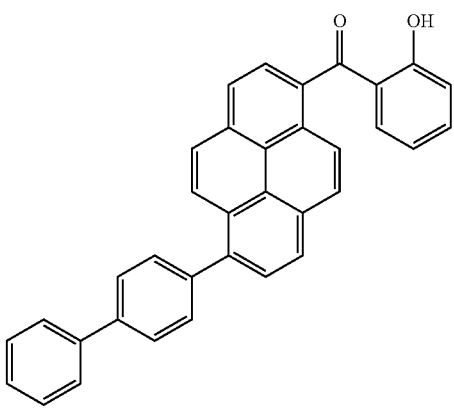

5
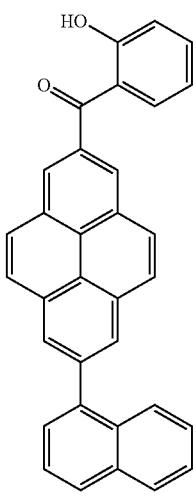

6
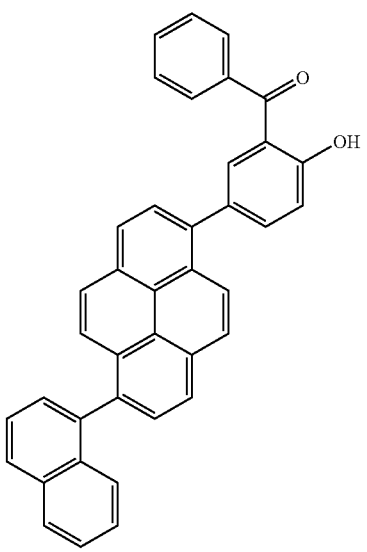

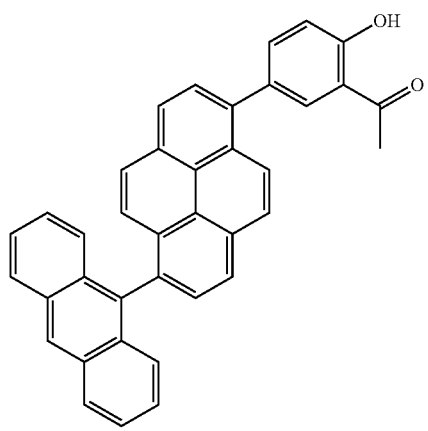
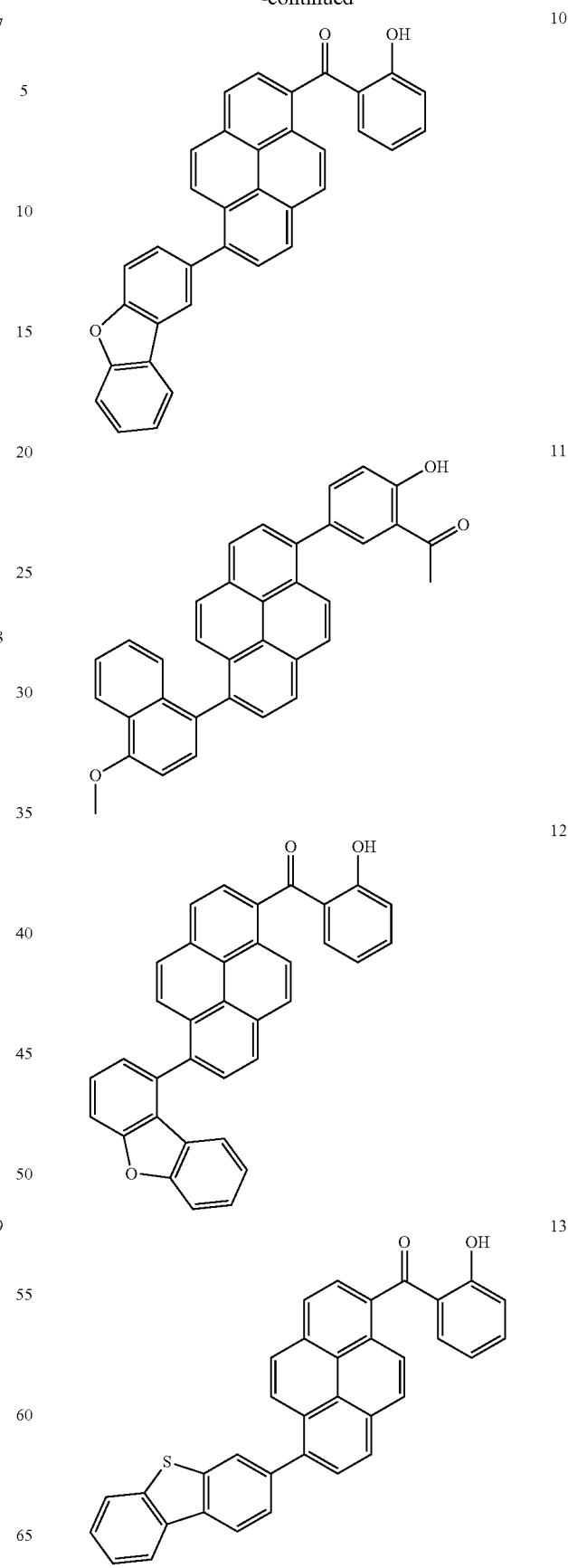

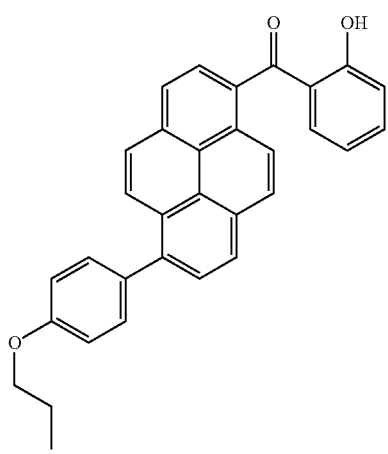
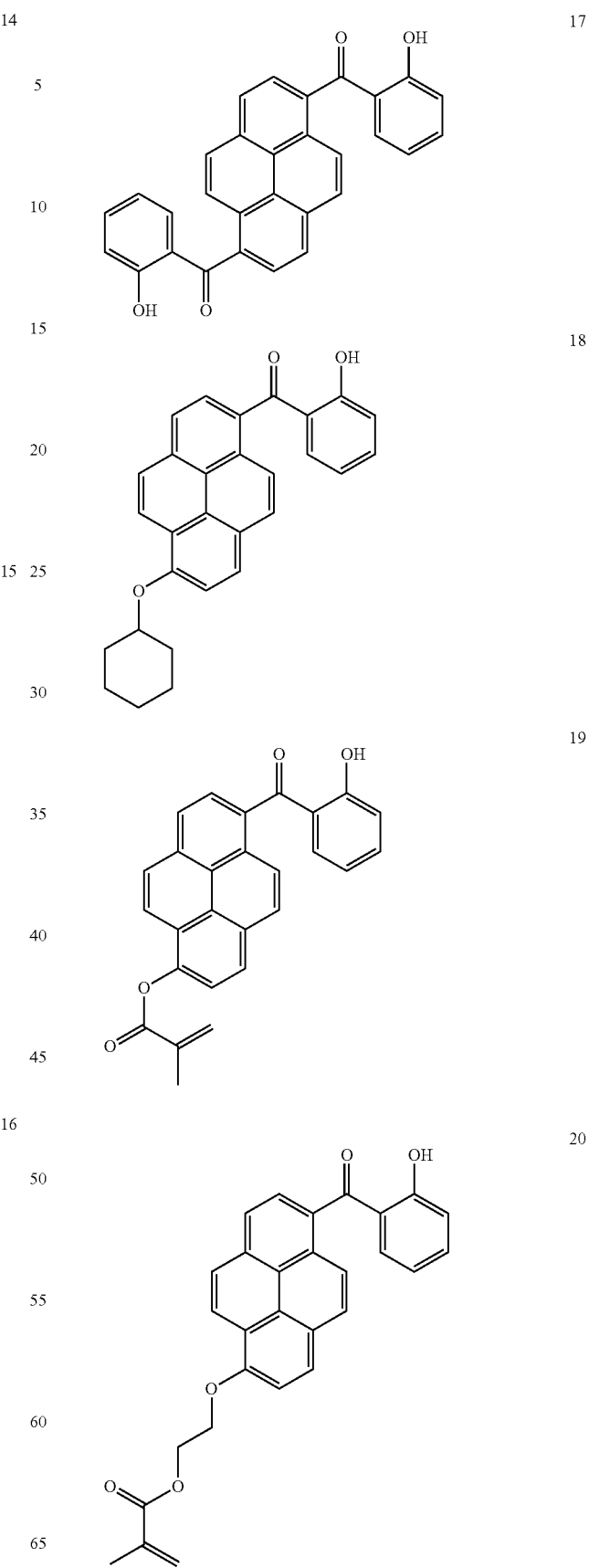

21
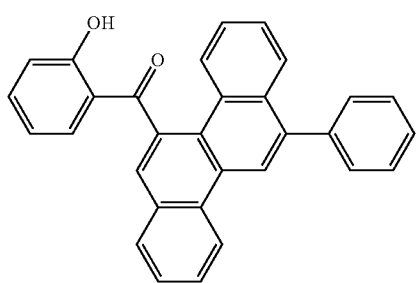
22
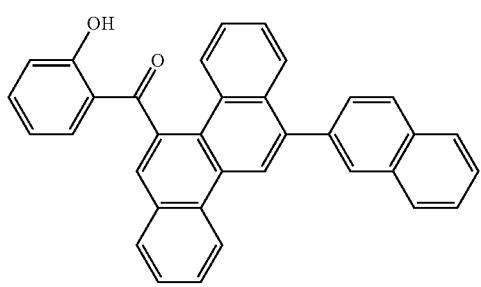
23
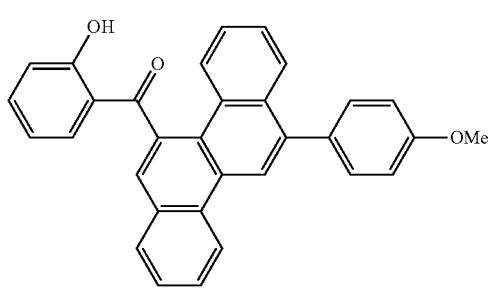
24
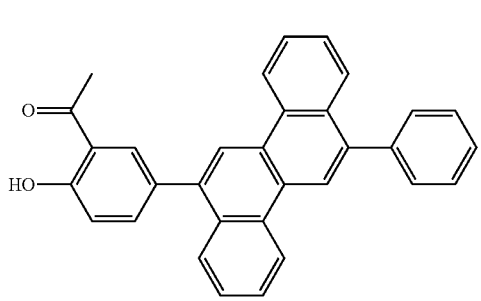
25
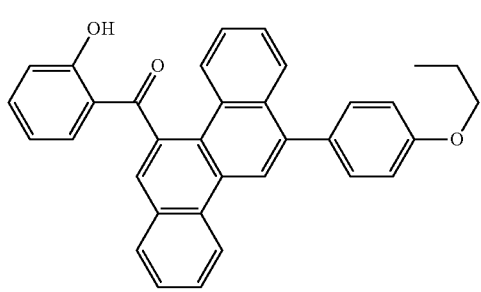
26
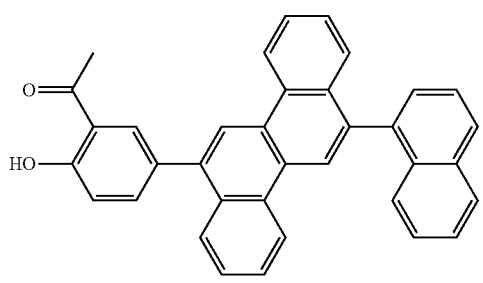
27
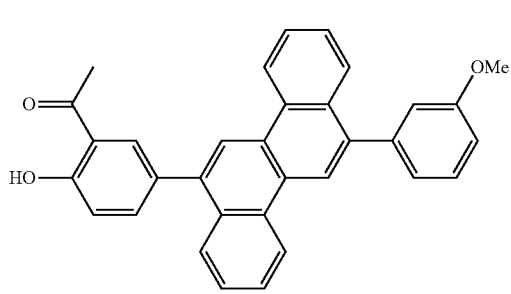
28
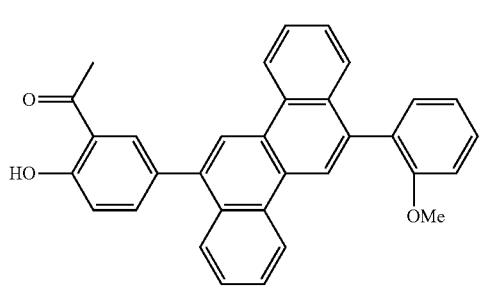
29
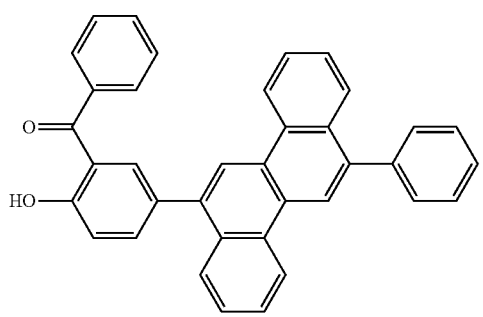
30
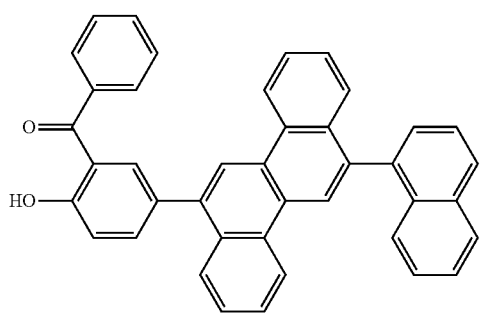

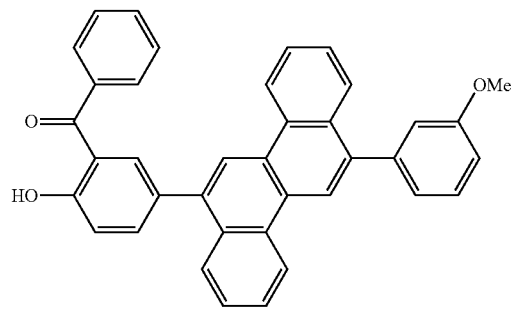
31
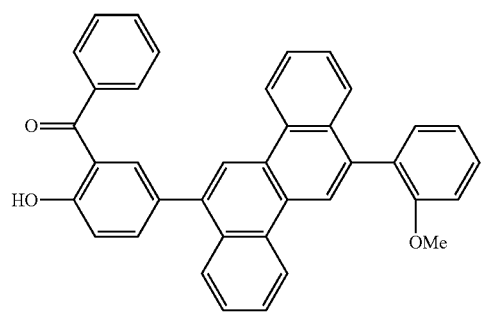
32
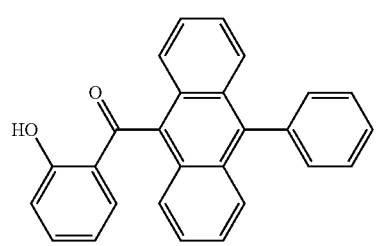
33
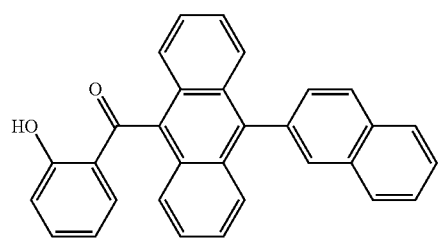
34
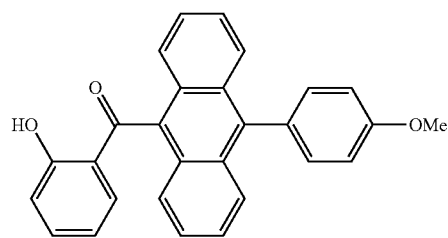
35
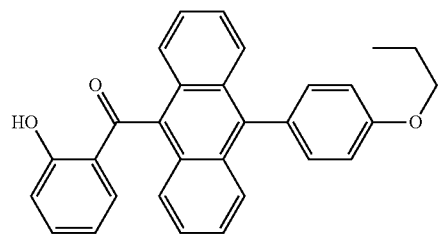
36
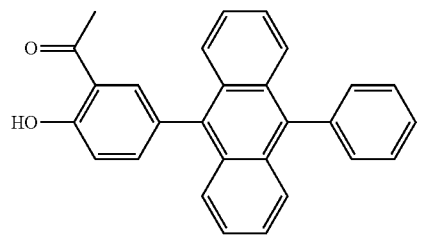
37
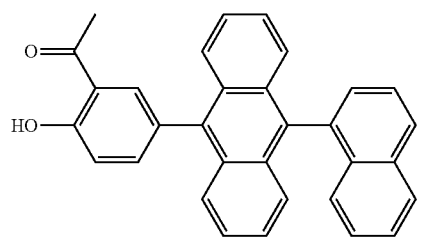
38
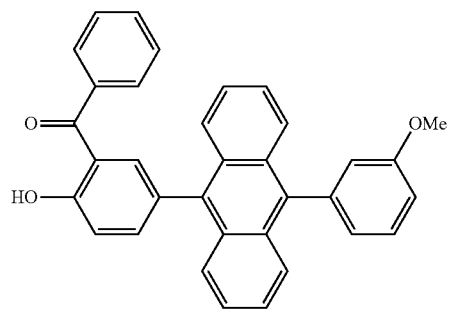
39
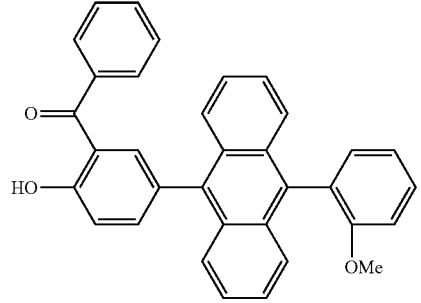
40
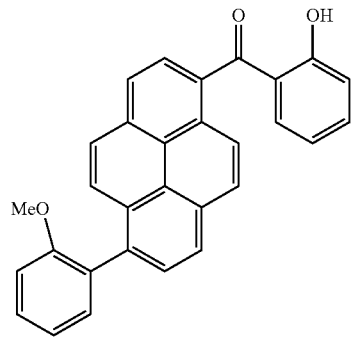
41

42

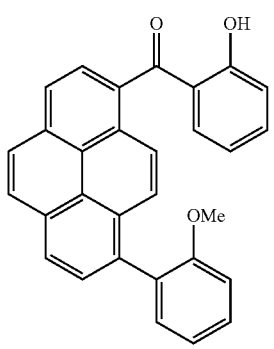

43

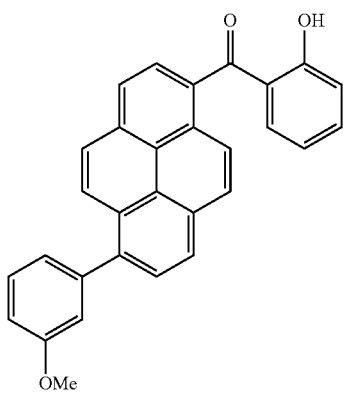

44

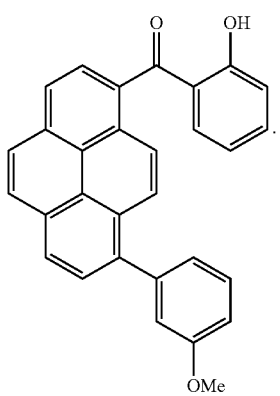

21. An organic electroluminescence device comprising:
a first electrode;
a hole transport region provided on the first electrode;
a light emitting layer provided on the hole transport region;
an electron transport region provided on the light emitting layer;
a second electrode provided on the electron transport region; and
a light absorbing layer provided on at least one of a lower portion of the first electrode or an upper portion of the second electrode, wherein the light absorbing layer comprises a light absorber including a polycyclic aromatic compound, and the polycyclic aromatic compound is substituted with a substituent including a structure represented by Formula A below:

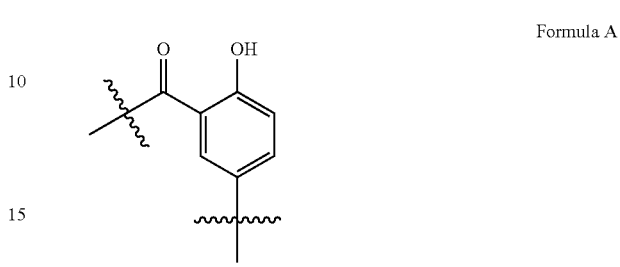

Formula A wherein in Formula A, are each independently a position substituted with the polycyclic aromatic compound or a position substituted with a hydrogen atom or a substituted or unsubstituted aryl group having 6 to 30 ring-forming carbon atoms, and wherein the polycyclic aromatic compound comprises pyrene, chrysene, or anthracene.

22. The organic electroluminescence device of claim 21, wherein the polycyclic aromatic compound is further substituted with a substituted or unsubstituted alkyl group having 1 to 20 carbon atoms, a substituted or unsubstituted alkenyl group having 2 to 20 carbon atoms, a substituted or unsubstituted alkoxy group having 1 to 20 carbon atoms, a substituted or unsubstituted acrylate group having 1 to 20 carbon atoms, a substituted or unsubstituted aryl group having 6 to 30 ring-forming carbon atoms, a substituted or unsubstituted heteroaryl group having 2 to 30 ring-forming carbon atoms, a substituted or unsubstituted carbonyl group, a substituted or unsubstituted benzophenone group, a substituted or unsubstituted benzoate group, or a substituted or unsubstituted salicylate.

23. The organic electroluminescence device of claim 21, wherein the polycyclic aromatic compound is further substituted with a substituent represented by Formula 3 below:

Formula 3 wherein in Formula 3, R is a substituted or unsubstituted alkyl group having 1 to 5 carbon atoms.

24. The organic electroluminescence device of claim 21, wherein the light absorber comprises at least one selected from the compounds represented by Compound group 1 below:
Compound group 1
1
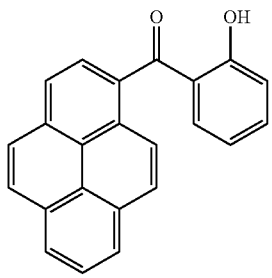
2
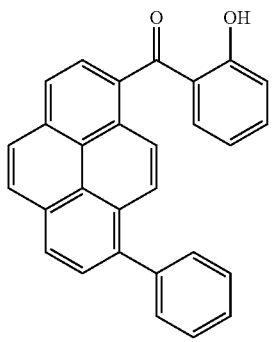
3
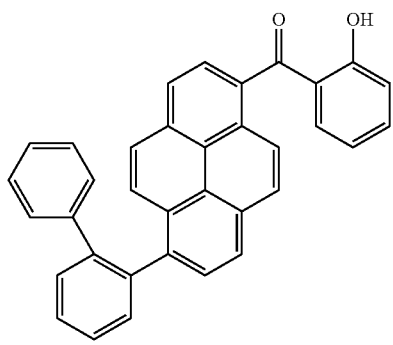
4
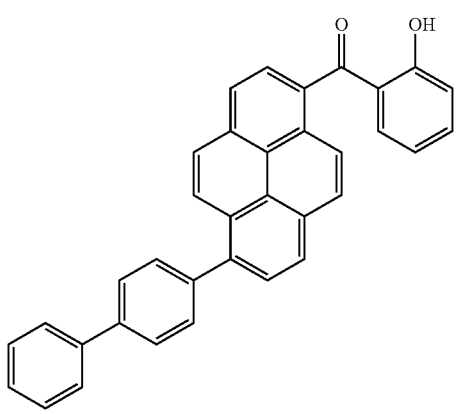
-continued
5
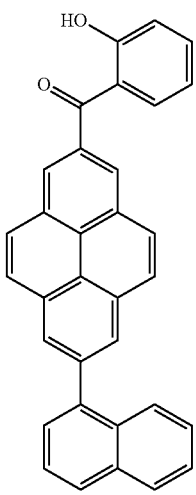
6
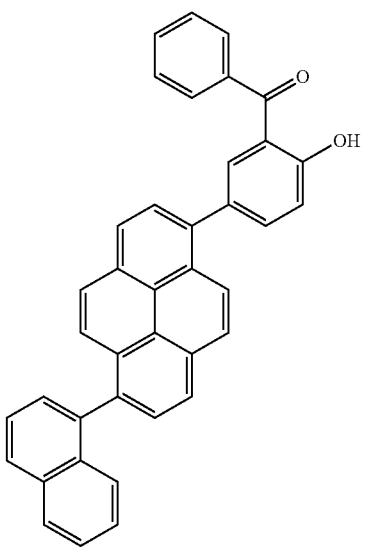
7
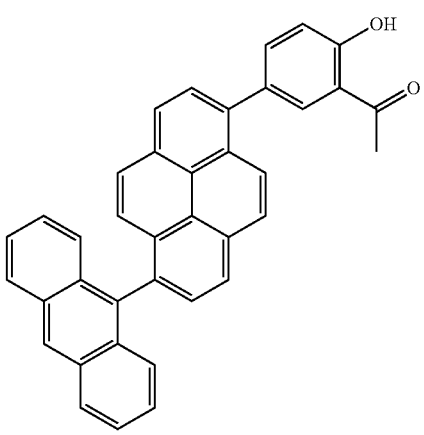

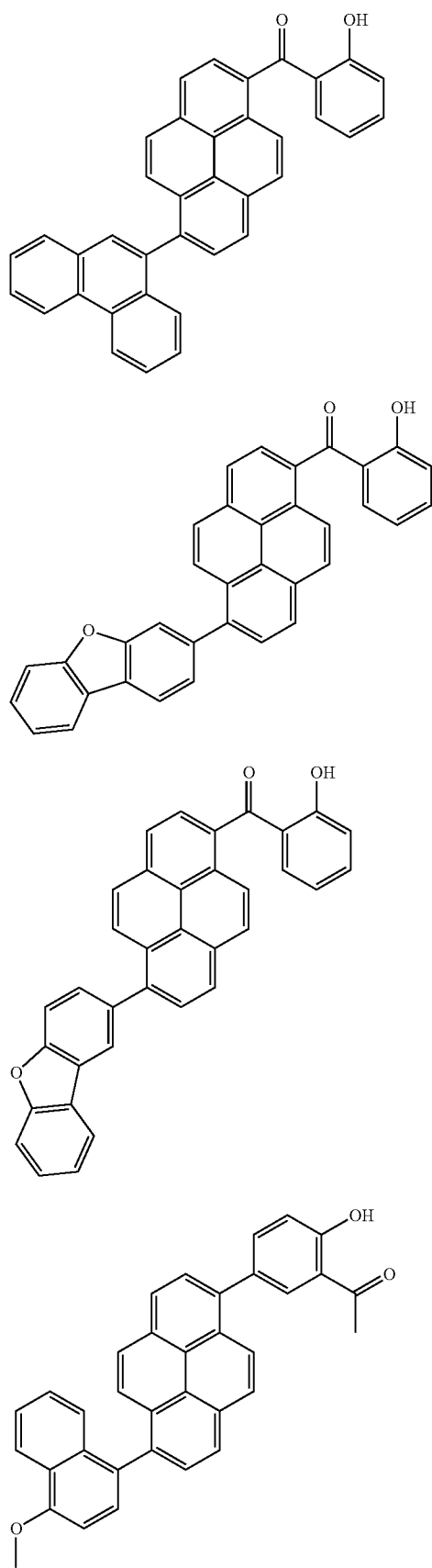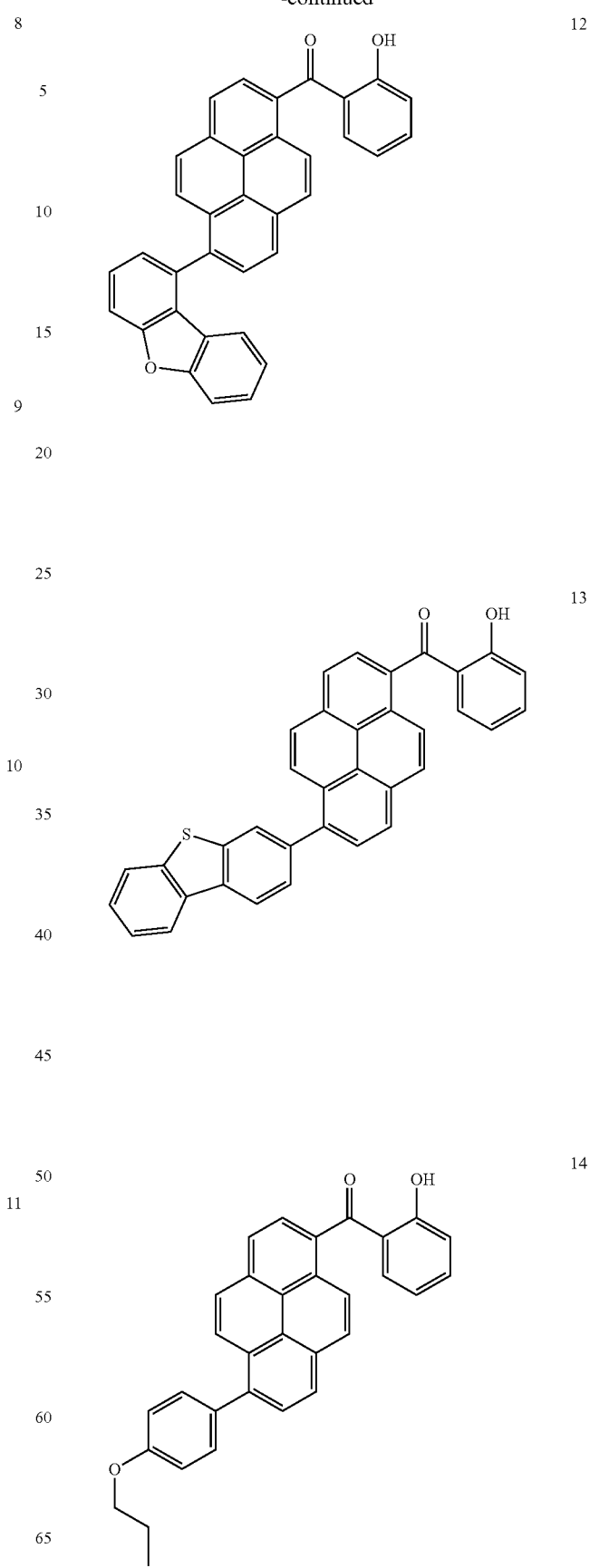

75
-continued
15
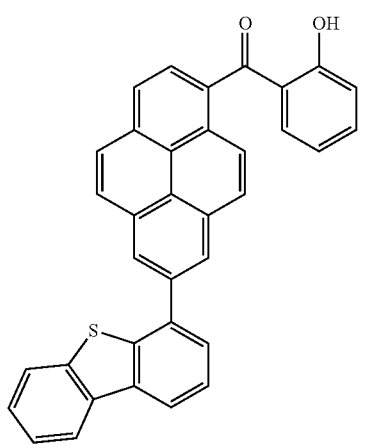
16
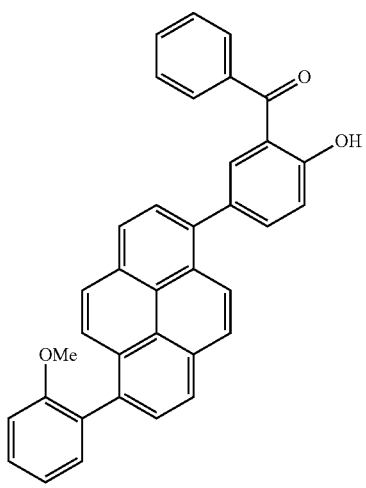
17
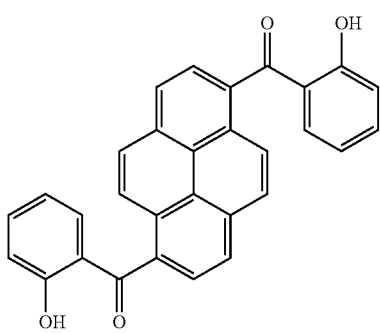
18
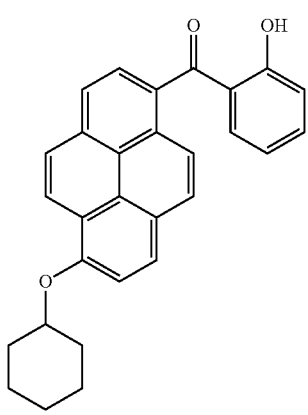
76
-continued
19
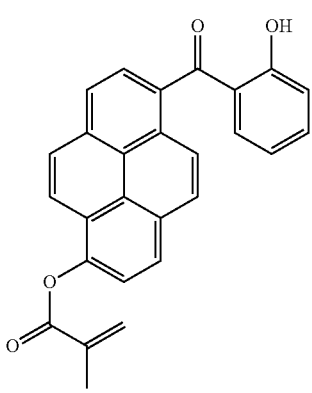
20
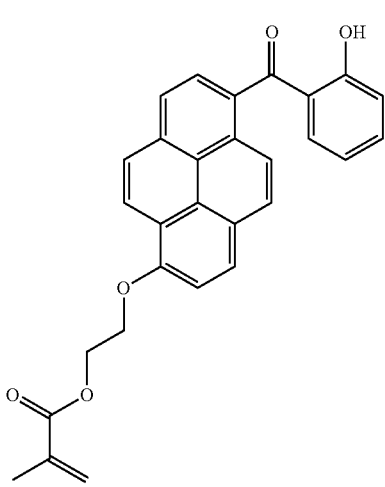
21
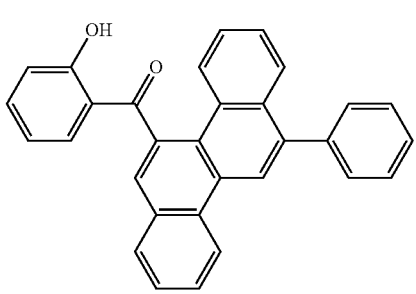
22
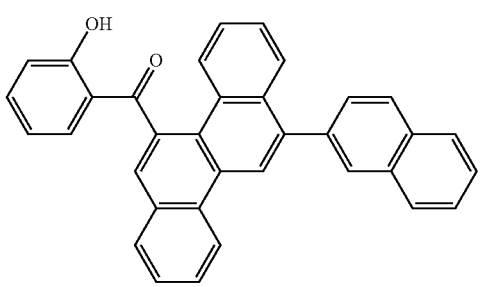

| 23 | 28 |
|---|---|
| 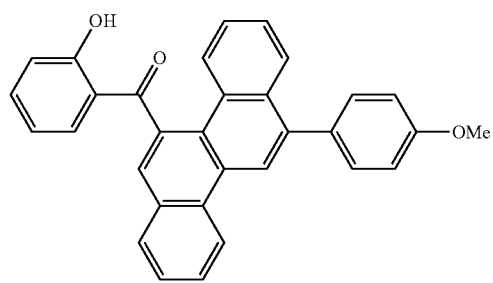 | 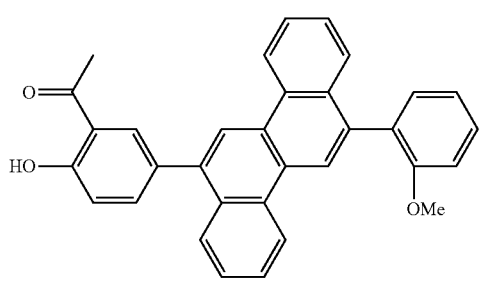 |
| 24 | 29 |
| 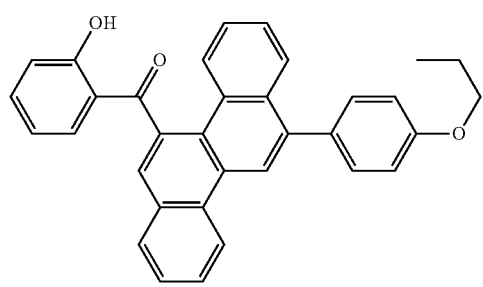 | 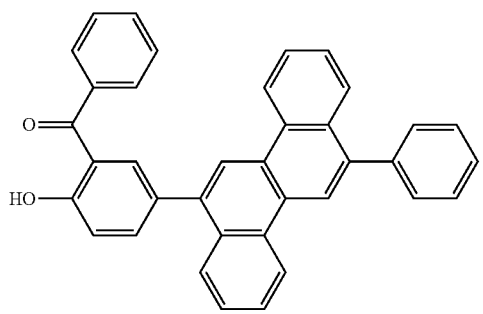 |
| 25 | 30 |
| 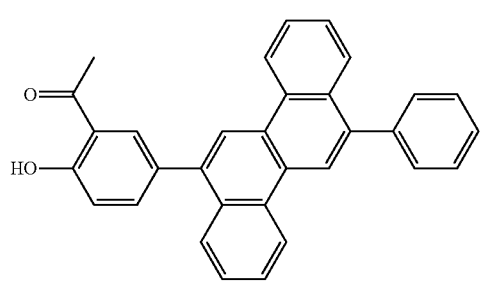 | 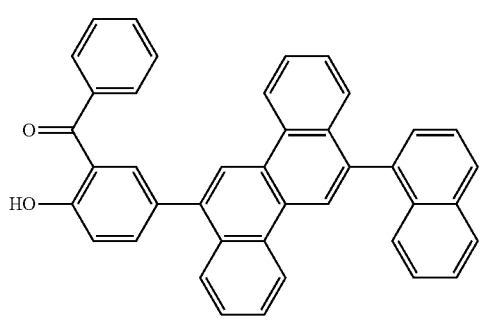 |
| 26 | 31 |
| 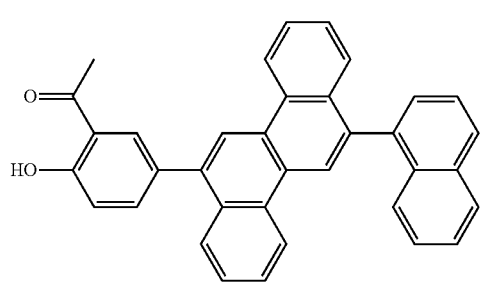 | 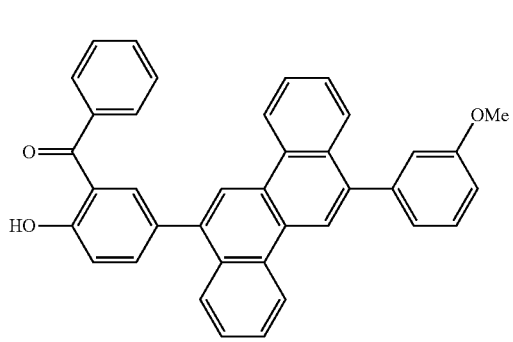 |
| 27 | 32 |
| 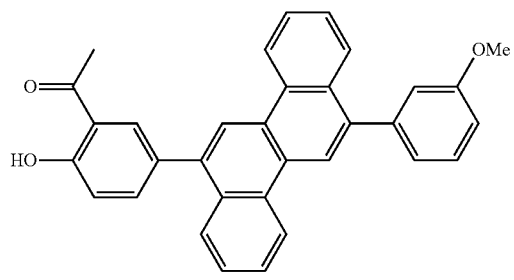 | 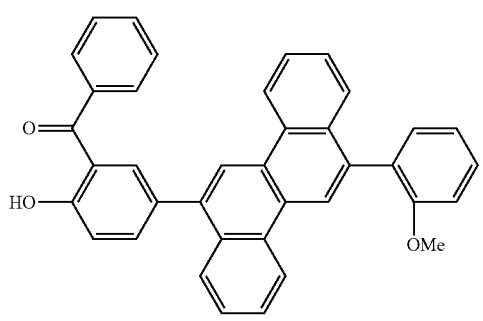 |

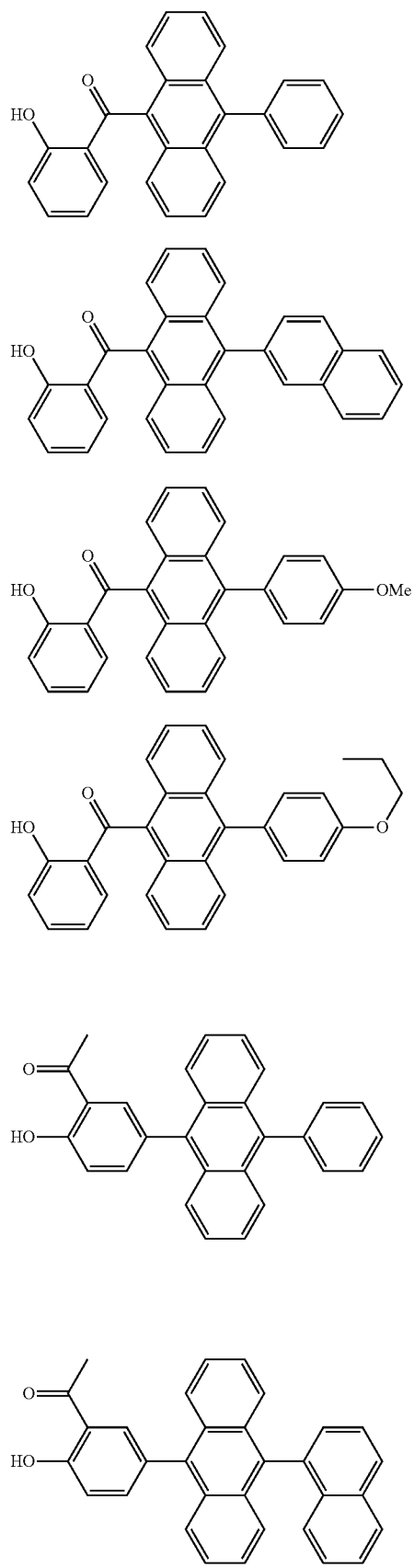
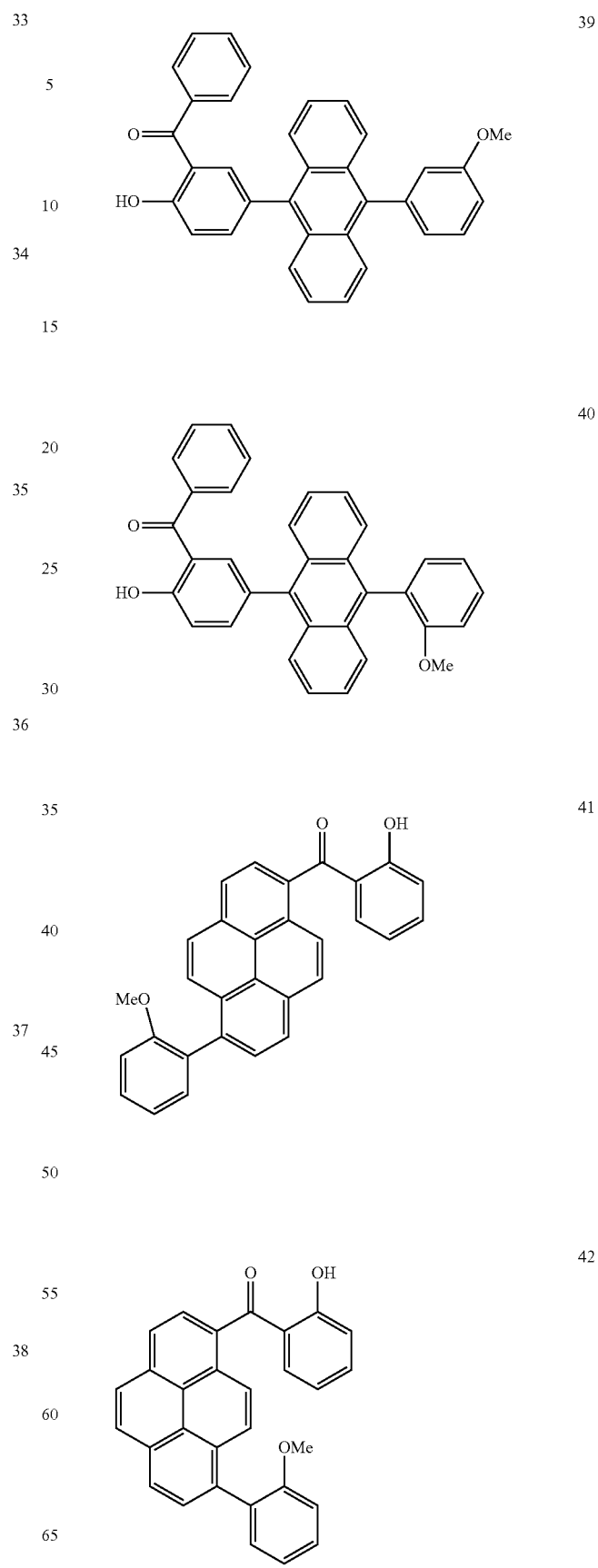

43
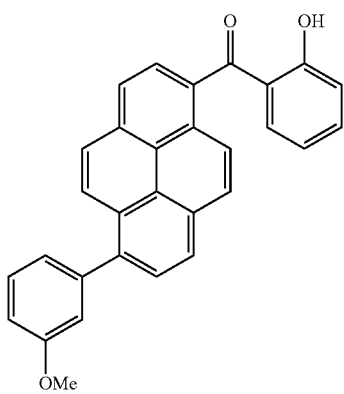
44
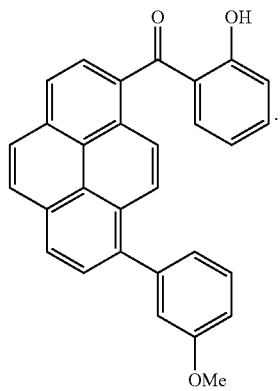
* * * * *